United States Patent
Burgey et al.

(10) Patent No.: US 6,455,532 B1
(45) Date of Patent: Sep. 24, 2002

(54) PYRAZINONE THROMBIN INHIBITORS

(75) Inventors: Christopher S. Burgey, Plymouth Meeting; Kyle A. Robinson, Elkins Park; Peter D. Williams, Harleysville; Craig Coburn, Royersford; Terry A. Lyle, Lederach; Philip E. Sanderson, Philadelphia, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/585,112

(22) Filed: Jun. 1, 2000

Related U.S. Application Data

(60) Provisional application No. 60/137,538, filed on Jun. 4, 1999, and provisional application No. 60/144,291, filed on Jul. 16, 1999.

(51) Int. Cl.[7] .................. A61K 31/497; C07D 401/12
(52) U.S. Cl. .................. 514/255.02; 544/405
(58) Field of Search .................. 544/405, 407, 544/409; 514/255.06, 255.05

(56) References Cited

U.S. PATENT DOCUMENTS

| | | | |
|---|---|---|---|
| 5,260,307 A | 11/1993 | Ackermann et al. | 514/323 |
| 5,405,854 A | 4/1995 | Ackermann et al. | 514/315 |
| 5,455,348 A | 10/1995 | Austel et al. | 544/238 |
| 5,459,142 A | 10/1995 | Tone et al. | 514/252 |
| 5,510,369 A | 4/1996 | Lumma et al. | 514/422 |
| 5,744,486 A | 4/1998 | Sanderson et al. | 514/318 |
| 5,866,573 A | 2/1999 | Sanderson et al. | 514/235.8 |
| 5,981,546 A | 11/1999 | Duggan et al. | 514/300 |

FOREIGN PATENT DOCUMENTS

| | | |
|---|---|---|
| EP | 0 262096 A1 | 3/1988 |
| EP | 0509769 A2 | 10/1992 |
| WO | WO 94/25051 | 11/1994 |
| WO | WO 96/11697 | 4/1996 |
| WO | WO 96/31504 | 10/1996 |
| WO | WO 96/32110 | 10/1996 |
| WO | WO 97/01338 | 1/1997 |
| WO | WO 97/40024 | 10/1997 |
| WO | WO 98/31670 | 7/1998 |
| WO | WO 98/42342 | 10/1998 |
| WO | WO 99/11267 | 3/1999 |
| WO | WO 99/59591 | 11/1999 |
| WO | WO 00/69834 | 11/2000 |

OTHER PUBLICATIONS

Peter R. Bernstein, et al., "Nonpeptidic Inhibitors of Human Leukocyte Elastase . . . "*J. Med. Chem.*, vol. 37, 1994, pp. 3313–3326.

Sanderson, et al., "Preparation of 3-amino-2-pyrazinone-1-acetamide derivatives as thrombin inhibitors," *Chem. Abstracts* (The Amer. Chem. Soc.), vol. 128, No. 3, pp. 532–533, 22922r, Jan. 19, 1998.

Kitazawa, et al.., "Preparation of 1,4-disubstituted cyclic amino derivatives as serotonin antagonists," Database CA on Stn., Chem Abs., vol. 129: 302552 (1998).

Semple et al., J. Med. Chem., vol. 39 (1996), p. 4531–4536, "Design, synthesis, and evolution of a novel, selective, and orally bioavailable class of thrombin inhibitors . . . ".

Sanderson, et al., Bioorganic & Medicinal Chemistry Letters, vol. 8 (1998), pp. 817–822, "L–374,087, An efficacious, orally bioavailable, pyridinone acetamide thrombin inhibitor".

*Primary Examiner*—Richard L. Raymond
(74) *Attorney, Agent, or Firm*—Melvin Winokur; Valerie J. Camara; Richard S. Parr

(57) ABSTRACT

Compounds of the invention are useful in inhibiting thrombin and associated thrombotic occlusions having the following structure:

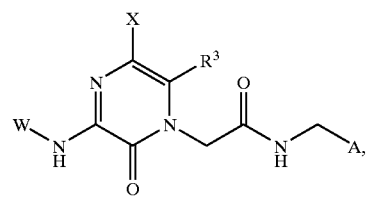

A is

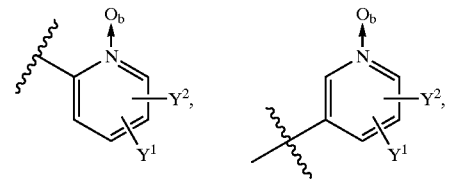

or

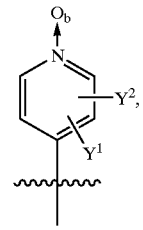

wherein $Y^1$ and $Y^2$ are independently
hydrogen,
$C_{1-4}$ alkyl,
$C_{1-4}$ alkoxy,
$F_uH_vC(CH_2)_{0-1}$ O—, wherein u and v are either 1 or 2, provided that when u is 1, v is 2, and when u is 2, v is 1,
$C_{3-7}$ cycloalkyl,
thio $C_{1-4}$ alkyl,
$C_{1-4}$ sulfinylalkyl,
$C_{1-4}$ sulfonylalkyl,
halogen
cyano, or
trifluoromethyl, and
wherein b is 0 or 1.

25 Claims, No Drawings

PYRAZINONE THROMBIN INHIBITORS

CROSS REFERENCE TO RELATED APPLICATIONS

This application claims the benefit of U.S. Provisional Application No. 60/137,538, filed Jun. 4, 1999 and U.S. Provisional Application No. 60/144,291, filed Jul. 16, 1999.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., J. Amer. Chem. Soc., (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., J. Med. Chem., Vol. 37, pages 1259–1261 (1994) describes orally active, non-peptidic inhibitors of human leukocyte elastase which contain trifluoromethylketone and pyridinone moieties.

H. Mack et al., J. Enzyme Inhibition, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

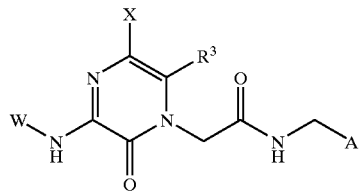

wherein
W is selected from the group consisting of
1) hydrogen,
2) a 5- to 7-membered mono- or a 9- to 10-membered fused bicyclic heterocyclic ring having carbon ring atoms and heteroatom ring atoms which ring can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
     i) $C_{1-4}$ alkyl,
     ii) hydroxy,
     iii) COOR', where R' is hydrogen or $C_{1-4}$ alkyl,
     iv) $CONH_2$,
     v) $CH_2OH$,
     i) $SO_2NH_2$,
     vii) halogen,
     viii) amino,
     ix) aryl,
     x) $C_{3-7}$ cycloalkyl,
     xi) $CF_3$,
     xii) $OCF_3$
     xiii) $N(CH_3)_2$,
     xiv) —$C_{1-3}$alkylaryl,
     xv) heterocyclic ring,
     xvi) $C_{1-4}$ alkoxy,
     xvii) $F_wH_xC(CH_2)_{0-1}$ O—, wherein w and x are either 1 or 2, provided that when w is 1, x is 2, and when w is 2, x is 1,
     xviii) $C_{1-4}$ thioalkoxy, or
     xix) cyano,
3) a 5- to 7-membered mono- or a 9- to 10-membered fused bicyclic non-heterocyclic saturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1, r) $C_{1-4}$ thioalkoxy, or s) cyano, 4) a 6-membered mono or 9- to 10-membered fused bicyclic non-heterocyclic unsaturated ring which is unsubstituted or substituted with one or more of a) $C_{1-4}$ alkyl, b) hydroxy, c) COOR', where R' is hydrogen or $C_{1-4}$ alkyl, d) $CONH_2$, e) $CH_2OH$, f) $SO_2NH_2$, g) halogen, h) amino, i) aryl, j) $C_{3-7}$ cycloalkyl, k) $CF_3$, l) $OCF_3$, m) $N(CH_3)_2$, n) —$C_{1-3}$ alkylaryl, o) heterocyclic ring, p) $C_{1-4}$ alkoxy, q) $F_w H_x C(CH_2)_{0-1} O$—, wherein w and x are either 1 or 2, provided that when w is 1, x is 2, and when w is 2, x is 1, r) $C_{1-4}$ thioalkoxy, or s) cyano,

5) $CF_3$,

6) $C_{3-7}$ cycloalkyl, unsubstituted, monosubstituted with halogen or aryl, or disubstituted with halogen, 7) $C_{7-12}$ bicyclic alkyl, 8) $C_{10-16}$ tricyclic alkyl,

9)

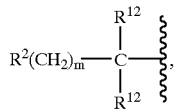

where m is 0–3, and each $R^{12}$ can be the same or different,

10)

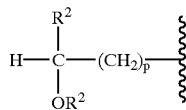

where p is 1–4,

11)

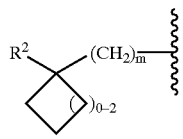

where m is 0–3,

12)

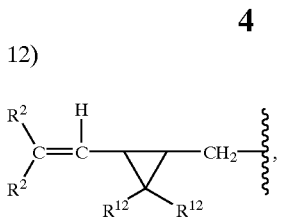

13)

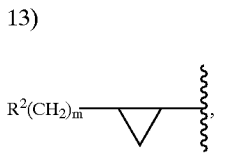

where m is 0 or 1,

14)

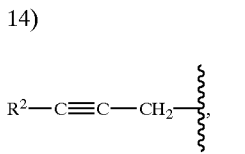

15)

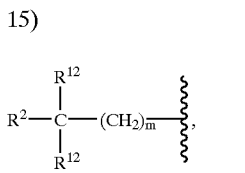

wherein m is 0–3, and each $R^{12}$ can be the same or different, wherein the $R^{12}$ substituents can together form a ring, with the C to which they are bonded, represented by $C_{3-7}$ cycloalkyl,

16)

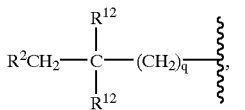

wherein q is 0–2, and each $R^{12}$ can be the same or different, wherein the $R^{12}$ substituents can together form a ring, with the C to which they are bonded, represented by $C_{3-7}$ cycloalkyl,

17)

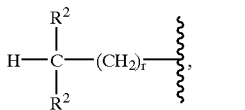

wherein r is 0-4, and each $R^2$ can be the same or different, wherein the $R^2$ substituents can together form a ring, with the C to which they are bonded, represented by $C_{3-7}$ cycloalkyl, $C_{7-12}$ bicyclic alkyl, $C_{10-16}$ tricyclic alkyl, or a 5- to 7-membered mono- or 9- to 10-membered fused bicyclic heterocyclic ring, which can be saturated or unsaturated, and which contains from one to three heteroatoms selected from the group consisting of N, O and S,

18)

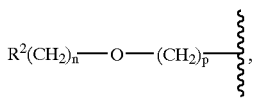

wherein n and p are independently 1–4,

19)

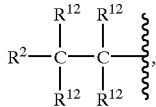

wherein each $R^{12}$ can be the same or different,

20)

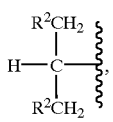

and

21)

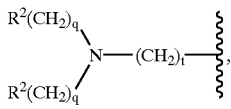

wherein t is 1–4 and q is independently 0–2;

$R^2$ is selected from the group consisting of
1) hydrogen,
2) a 5- to 7-membered mono- or a 9- to 10-membered fused bicyclic heterocyclic ring having carbon ring atoms and heteroatom ring atoms which can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
      i) $C_{1-4}$ alkyl,
      ii) hydroxy,
      iii) COOR', where R' is hydrogen or $C_{1-4}$ alkyl,
      iv) $CONH_2$,
      v) $CH_2OH$,
      vi) $SO_2NH_2$,
      vii) halogen,
      viii) amino,
      ix) aryl,
      x) $C_{3-7}$ cycloalkyl,
      xi) $CF_3$,
      xii) $OCF_3$,
      xiii) $N(CH_3)_2$,
      xiv) —$C_{1-3}$alkylaryl,
      xv) heterocyclic ring,
      xvi) $C_{1-4}$ alkoxy,
      xvii) $F_wH_xC(CH_2)_{0-1}$ O—, wherein w and x are either 1 or 2, provided that when w is 1, x is 2, and when w is 2, x is
      xviii) $C_{1-4}$thioalkoxy, or
      xix) cyano,
3) a 5- to 7-membered mono- or a 9- to 10-membered fused bicyclic non-heterocyclic saturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, xis 1,
   r) $C_{1-4}$ thioalkoxy, or
   s) cyano,
4) a 6-membered mono or 9- to 10-membered fused bicyclic non-heterocyclic unsaturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1,
   r) $C_{1-4}$ thioalkoxy, or
   s) cyano,
5) $C_{1-7}$ alkyl, unsubstituted or substituted with one or more of
   a) hydroxy,
   b) COOH,
   c) halogen,
   d) amino,
   e) aryl,
   f) $C_{3-7}$ cycloalkyl,
   g) $CF_3$,
   h) $N(CH_3)_2$,
   i) —$C_{1-3}$alkylaryl,
   j) heterocyclic ring,
   k) $C_{1-4}$ alkoxy,
   l) $C_{1-4}$ thioalkoxy, or
   m) cyano,
6) $CF_3$,
7) $C_{3-7}$ cycloalkyl, unsubstituted, monosubstituted with halogen or aryl, or disubstituted with halogen,
8) $C_{7-12}$ bicyclic alkyl, and
9) $C_{10-16}$ tricyclic alkyl;

R³ and X are independently selected from the group consisting of
1) hydrogen,
2) halogen,
3) cyano,
4) C₁₋₄ alkylthio,
5) C₁₋₄ alkylsulfinyl,
6) C₁₋₄ alkylsulfonyl,
7) C₁₋₄ alkyl,
8) C₃₋₇ cycloalkyl, and
9) trifluoromethyl;

A is

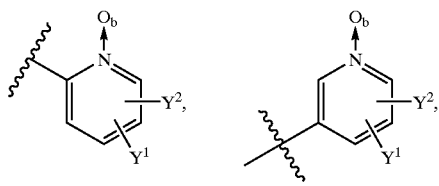

or

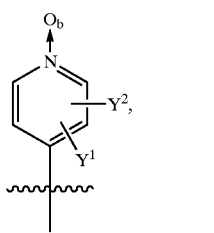

wherein Y¹ and Y² are independently selected from the group consisting of
1) hydrogen,
2) C₁₋₄ alkyl,
3) C₁₋₄ alkoxy,
4) F$_u$H$_v$C(CH₂)$_{0-1}$ O—, wherein u and v are either 1 or 2, provided that when u is 1, v is 2, and when u is 2, v is 1,
5) C₃₋₇ cycloalkyl,
6) C₁₋₄ alkylthio,
7) C₁₋₄ alkylsulfinyl,
8) C₁₋₄ alkylsulfonyl,
9) halogen
10) cyano, and
11) trifluoromethyl, and
wherein b is 0 or 1; and R¹² is selected from the group consisting of
1) hydrogen,
2) halogen,
3) a 5- to 7-membered mono- or a 9- to 10-membered fused bicyclic heterocyclic ring having carbon ring atoms and heteroatom ring atoms which ring can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
      i) C₁₋₄ alkyl,
      ii) hydroxy,
      iii) COOR', where R' is hydrogen or C₁₋₄ alkyl,
      iv) CONH₂,
      v) CH₂OH,
      vi) SO₂NH₂,
      vii) halogen,
      viii) amino,
      ix) aryl,
      x) C₃₋₇ cycloalkyl,
      xi) CF₃,
      xii) OCF₃,
      xiii) N(CH₃)₂,
      xiv) —C₁₋₃alkylaryl,
      xv) heterocyclic ring,
      xvi) C₁₋₄ alkoxy,
      xvii) F$_w$H$_x$C(CH₂)$_{0-1}$ O—, wherein w and x are either 1 or 2, provided that when w is 1, x is 2, and when w is 2, x is 1,
      xviii) C₁₋₄ thioalkoxy, and
      xix) cyano,
4) a 5- to 7-membered mono- or a 9- to 10-membered fused bicyclic non-heterocyclic saturated ring which is unsubstituted or substituted with one or more of
   a) C₁₋₄ alkyl,
   b) hydroxy,
   c) COOR', where R' is hydrogen or C₁₋₄ alkyl,
   d) CONH₂,
   e) CH₂OH,
   f) SO₂NH₂,
   g) halogen,
   h) amino,
   i) aryl,
   j) C₃₋₇ cycloalkyl,
   k) CF₃,
   l) OCF₃,
   m) N(CH₃)₂,
   n) —C₁₋₃alkylaryl,
   o) heterocyclic ring,
   p) C₁₋₄ alkoxy,
   q) F$_w$H$_x$C(CH₂)$_{0-1}$ O—, wherein w and x are either 1 or 2, provided that when w is 1, x is 2, and when w is 2, x is 1,
   r) C₁₋₄ thioalkoxy, or
   s) cyano,
5) a 6-membered mono or 9- to 10-membered fused bicyclic non-heterocyclic unsaturated ring which is unsubstituted or substituted with one or more of
   a) C₁₋₄ alkyl,
   b) hydroxy,
   c) COOR', where R' is hydrogen or C₁₋₄ alkyl,
   d) CONH₂,
   e) CH₂OH,
   f) SO₂NH₂,
   g) halogen,
   h) amino,
   i) aryl,
   j) C₃₋₇ cycloalkyl,
   k) CF₃,
   l) OCF₃,
   m) N(CH₃)₂,
   n) —C₁₋₃alkylaryl,
   o) heterocyclic ring,
   p) C₁₋₄ alkoxy,
   q) F$_w$H$_x$C(CH₂)$_{0-1}$ O—, wherein w and x are either 1 or 2, provided that when w is 1, x is 2, and when w is 2, x is 1,
   r) C₁₋₄ thioalkoxy, or
   s) cyano,
6) biphenyl,
7) CF₃,
8) C₃₋₇ cycloalkyl, 9) $C_{7-12}$ bicyclic alkyl, and
10) $C_{10-16}$ tricyclic alkyl;
or a pharmaceutically acceptable salt thereof.

In a class of compounds, $Y^1$ and $Y^2$ are independently selected from the group consisting of hydrogen, $C_{1-4}$ alkyl, halogen, $C_{1-4}$ alkylthio, $C_{1-4}$ alkylsulfinyl, $C_{1-4}$ alkylsulfonyl, and $C_{1-4}$ alkoxy.

In a subclass of the class of compounds, $Y^1$ and $Y^2$ are independently selected from the group consisting of hydrogen, F, $CH_3$, $SCH_3$, $SOCH_3$, $SO_2CH_3$, and $OCH_3$.

In a group of the subclass of compounds, A is selected from the group consisting of

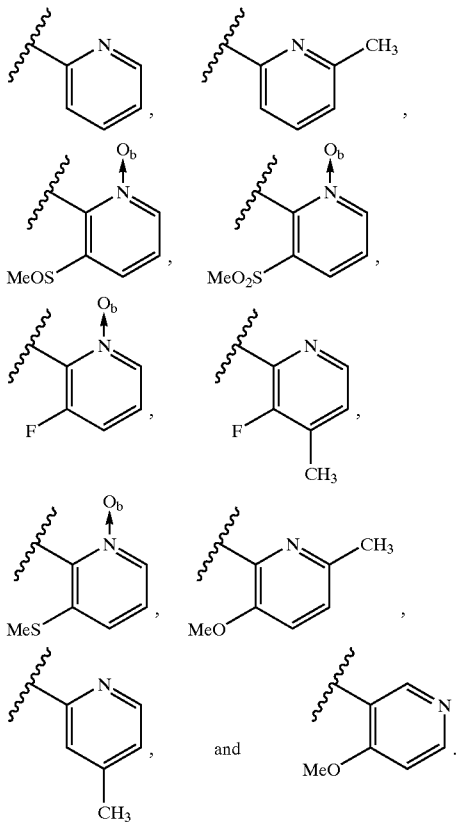

where b is 0 or 1.

In a subgroup of the group of compounds, X is hydrogen, $R^3$ is $CH_3$, Cl, or CN, and W is $R^2CF_2C(R^{12})_2$ or $R^2CH_2C(R^{12})_2$.

In a family of the subgroup of compounds, $R^{12}$ is hydrogen.

In a subfamily of the family of compounds, $R^2$ is selected from the group consisting of
1) a 5- to 7-membered mono- or a 9- to 10-membered fused bicyclic heterocyclic ring having carbon ring atoms and heteroatom ring atoms which ring can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
      i) $C_{1-4}$ alkyl,
      ii) hydroxy,
      iii) COOR', where R' is hydrogen or $C_{1-4}$ alkyl,
      iv) $CONH_2$,
      v) $CH_2O$ H,
      vi) $SO_2NH_2$,
      vii) halogen,
      viii) amino,
      ix) aryl,
      x) $C_{3-7}$ cycloalkyl,
      xi) $CF_3$,
      xii) $OCF_3$,
      xiii) $N(CH_3)_2$,
      xiv) —$C_{1-3}$alkylaryl,
      xv) heterocyclic ring,
      xvi) $C_{1-4}$ alkoxy,
      xvii) $F_wH_xC(CH_2)_{0-1}$ O—, wherein w and x are either 1 or 2, provided that when w is 1, x is 2, and when w is 2, x is 1,
      xviii) $C_{1-4}$ thioalkoxy, or
      xix) cyano, and
2) a 6-membered mono or 9- to 10-membered fused bicyclic non-heterocyclic unsaturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1,
   r) $C_{1-4}$ thioalkoxy, or
   s) cyano.

In a sub-subfamily of the subfamily of compounds, $R^2$ is pyridyl, methoxypyridyl, or phenyl.

Examples of the family are listed below (note that methyl substituents are conventionally indicated as bonds attached to an atom). Inhibitory activity of compounds of the invention is represented by "**", indicating Ki greater than or equal to 1 nM, or "*", indicating Ki less than 1 nM. Values are as determined according to the in vitro assay described later in the specification.

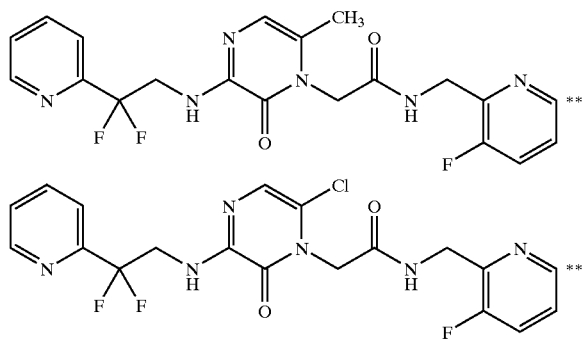

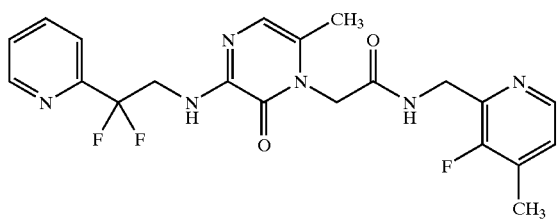
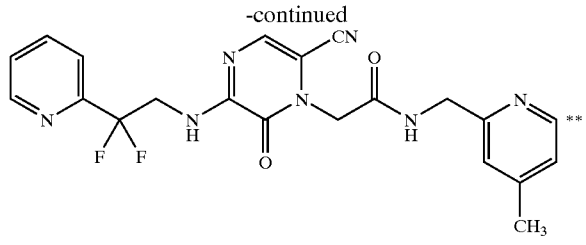
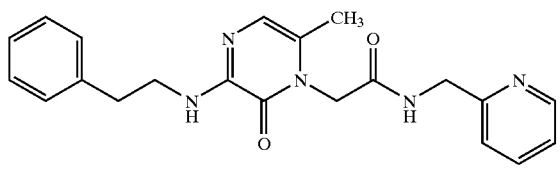
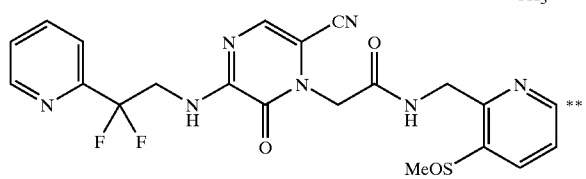
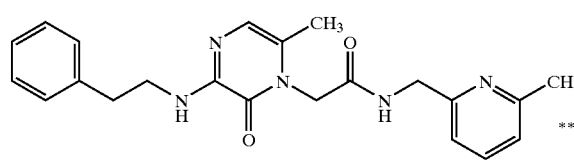
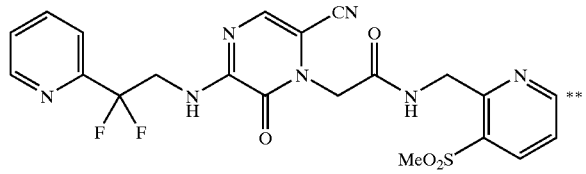
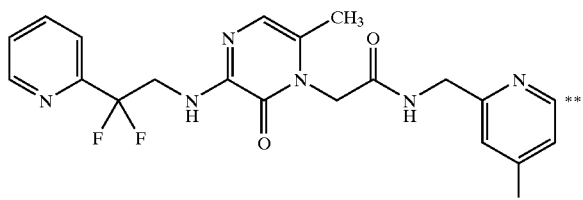
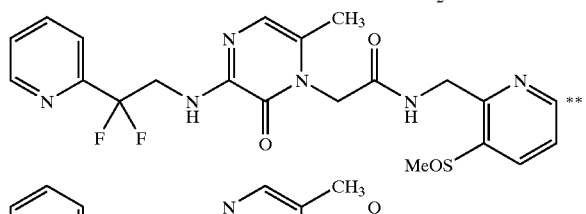
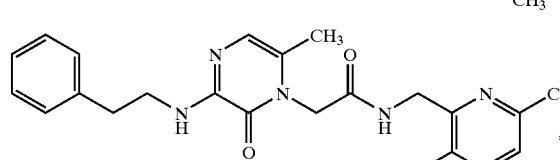
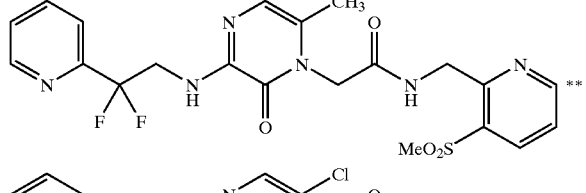
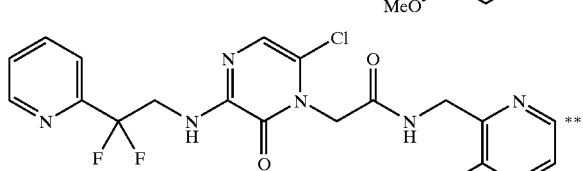
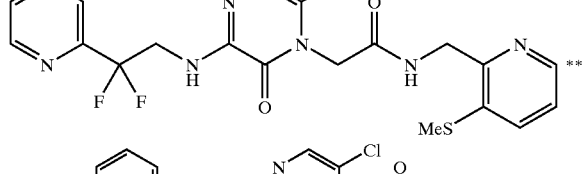
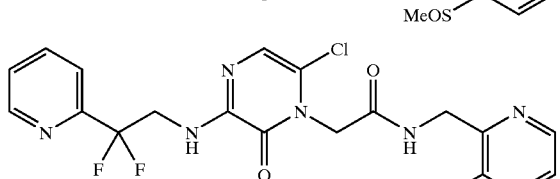
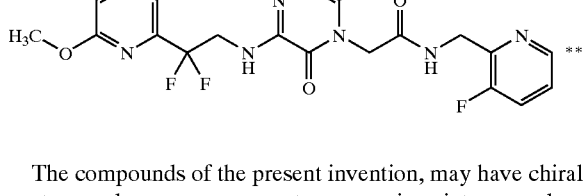
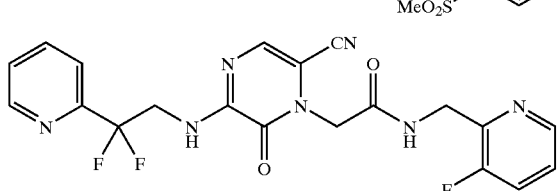
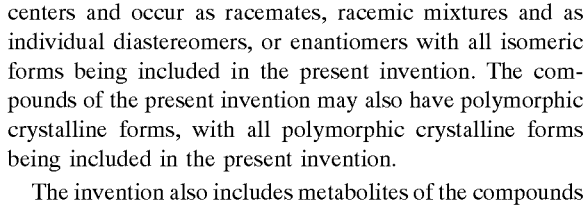
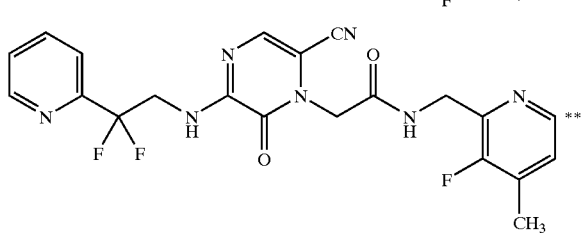

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

The invention also includes metabolites of the compounds of the invention, including the following compounds:

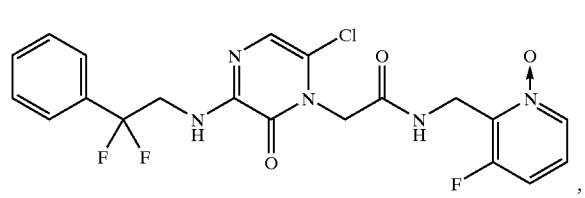

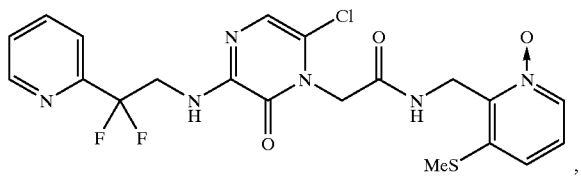

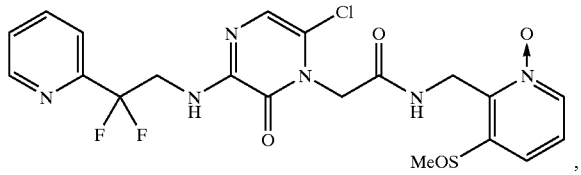

and

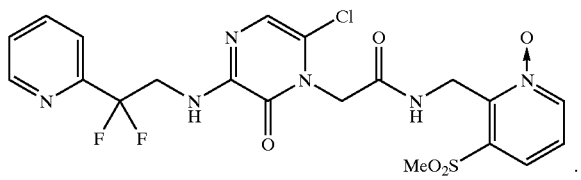

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows.

| ABBREVIATIONS | |
|---|---|
| BH₄ | borohydride |
| CH₂Cl₂ | dichloromethane |
| DAST | diethylaminosulfurtrifluoride |
| DBU | 1,8-diazabicyclo[5,4.0]undec-7-ene |
| DCE | 1,2-dichloroethane |
| DMF | dimethylformamide |
| DMSO | dimethylsulfoxide |
| DPPA | diphenylphosphoryl azide |
| EDC | 1-ethyl-3-(3-dimethylaminopropyl) carbodiimide hydrochloride |
| Et₂O | diethyl ether |
| Et₃N | triethylamine |
| EtOH | ethanol |
| HCl | hydrochloric acid |
| HOBT | 1-hydroxybenzotriazole hydrate |
| HOAT | 1-hydroxy-7-azabenzotriazole |
| iPrOH | 2-propanol |
| LDA | lithium diisopropylamide |
| LiAlH₄ | lithium aluminum hydride |
| MeI | iodomethane |
| MeOH | methanol |
| MCPBA | m-chloroperoxybenzoic acid |
| NaBH₄ | sodium borohydride |
| NaN₃ | sodium azide |
| NaSMe | sodium thiomethoxide |
| nBuLi | n-butyllithium |
| NCS | N-chlorosuccinimide |
| NMM | N-methylmorpholine |
| Pd/C | palladium on activated carbon catalyst |
| PhCH₃ | toluene |
| Ph₃P | triphenylphosphine |
| POBr₃ | phosphorous oxybromide |
| TBAF | tetrabutylammonium fluoride |
| TBSCl | tert-butyldimethylsilyl chloride |
| TEA | triethylamine |
| THF | tetrahydrofuran |
| TMSCN | trimethylsilyl cyanide |

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc.; "alkoxy" represents a linear or branched alkyl group of indicated number of carbon atoms attached through an oxygen bridge; "Halo", or "halogen", as used herein, means fluoro (F), chloro (Cl), bromo (Br) and iodo (I); and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl (bornyl), and the like.

The term "aryl" as used herein except where noted, represents a stable 6- to 10-membered mono- or bicyclic ring system such as phenyl, or naphthyl. The aryl ring can be unsubstituted or substituted with one or more of $C_{1-4}$ lower alkyl, hydroxy, alkoxy, halogen or amino.

The term "alkylaryl", e.g., $C_{1-3}$ alkylaryl, represents an aryl group having an alkyl substituent.

The term "biphenyl" means a ring assembly of two benzene rings, e.g.,

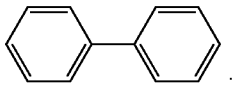

The term "heterocyclic ring", as used herein except where noted, represents a stable 5- to 7-membered monocyclic- or stable 9- to 10-membered fused bicyclic heterocyclic ring system any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

The term "non-heterocyclic ring", as used herein, except where noted, represents a stable 5- to 7-membered monocyclic, or stable 9- to 10-membered bicyclic ring system having carbon ring atoms and zero hetero ring atoms, which may be saturated, such cyclohexyl, partially saturated, or unsaturated, such as phenyl. Examples of such non-heterocyclic rings include phenyl, naphthylenyl, indenyl and cyclohexyl.

"Inhibitor of cyclooxygenase-2", "cyclooxygenase-2 inhibitor" and "COX-2 inhibitor" as used herein embrace compounds which selectively inhibit cyclooxygenase-2 over cyclooxygenase-1.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

In compounds of the invention having pyridyl N-oxide moieties, the pyridyl-N-oxide portion is structurally depicted using conventional representations such as

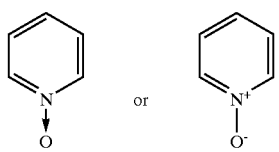

which have equivalent meanings.

In the definition of variable "A", when variable "b" is zero, A is

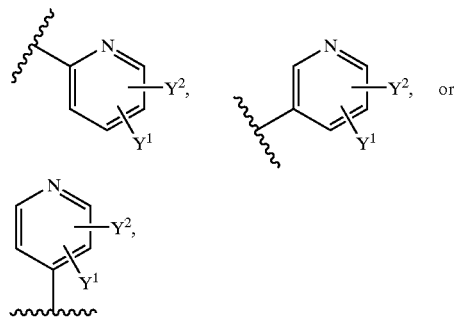

When variable "b" is 1, A is

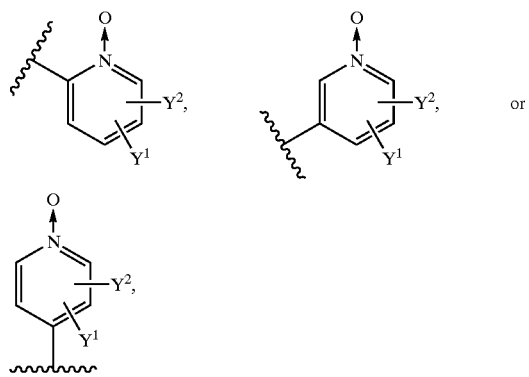

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Coming Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025 mg/kg/day to 7.5 mg/kg/day, more preferably 0.1 mg/kg/day to 2.5 mg/kg/day, and most preferably 0.1 mg/kg/day to 0.5 mg/kg/day (unless specificed otherwise, amounts of active ingredients are on free base basis). For example, an 80 kg patient would receive between about 0.8 mg/day and 2.4 g/day, preferably 2 mg/day to 600 mg/day, more preferably 8 mg/day to 200 mg/day, and most preferably 8 mg/day to 40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 1.2 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The invention also includes a method for treating an inflammatory disease in a patient which comprises treating the patient with a composition comprising a compound of the present invention. Such diseases include but are not limited to nephritis, systemic lupus erythematosus, rheumatoid arthritis, glomerulonephritis, and sacoidosis.

The invention is also a method for treating an inflammatory disease in a patient that comprises treating the patient with a combination comprising a compound of the invention and an NSAID, e.g., a COX-2 inhibitor. Such diseases include but are not limited to nephritis, systemic lupus, erythematosus, rheumatoid arthritis, glomerulonephritis, vasculitis and sacoidosis.

The present invention is a method for relieving pain, fever and inflammation of a variety of conditions including nephritis, systemic lupus erythematosus, rheumatoid arthritis, glomerulonephritis, sacoidosis, rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures in a patient by administering to the patient a therapeutically effective amount of a compound of the invention. Thrombin inhibitors may also be useful for the treatment of dementia including pre-senile and senile dementia, and in particular, dementia associated with Alzheimer Disease.

In inflammatory diseases wherein fibrin formation is prominent, the fibrin may be a determinant of the pathology. Fibrin serves as a matrix onto which inflammatory cells can migrate and adhere. (see Sherman et al., 1977 *J. Exp. Med.* 145:76–85; Altieri et al., 1986 *J. Clin. Invest.* 78:968–976; Wright et al., 1983 *Proc. Natl. Acad. Sci.* 85:7734–7738; Altieri et al., 1993 *J. Biol. Chem.* 268;1847–1853). Fibrin also enhances expression of the inflammatory cytokine IL-1beta and decreases expression of IL-1 receptor antagonist by human peripheral blood mononuclear cells (see Perez 1995 *J. Immunol.* 154:1879–1887). The anticoagulants warfarin and heparin attenuate delayed-type hypersensitivity reactions and experimental nephritis in animals. (see Jasain et al., Immunopathogenesis of Rheumatoid Arthritis Eds. G. S. Panayi et al., Surrey, UK, Reedbooks, Ltd. and Halpern et al., 1965 *Nature* 205:257–259). Enzymatic defibrination with ancrod diminishes the degree of experimental nephritis (Naish et al., 1972 *Clin. Sci.* 42:643–646), systemic lupus erythematosus (Cole et al., 1990 *Kidney Int.* 37:29–35, and rheumatoid arthritis (see Busso et al., 1998 *J. Clin. Invest.* 102:41–50) in animals, and glomerulonephritis in man (see Kim et al., 1988 *Q. J. Med.* 69:879–905). Additionally, intra articular injection of fibrin induces arthritis in rabbits immunized with fibrin Dumonde et al., 1961 *British Journal of Experimental Pathology* XLIII:373–383), and antigen-induced arthritis in mice is exacerbated in urokinase-deficient mice wherein fibrinolysis synovial fibrin is compromised (see Busso et al., 1998 *J. Clin. Invest.* 102:41–50).

In diseases where fibrin deposition is prominent such as, but not limited to, rheumatoid arthritis, systemic lupus erythematosus, glomerulonephritis, vasculitis and sacoidosis, lowering the steady state concentration of fibrin by administration of a compound of the invention will, according to the instant invention, diminish the pathological inflammatory responses associated with these diseases.

Similarly, compounds of the invention will be useful as a partial or complete substitute for conventional NSAIDs in preparations wherein they are presently co-administered with other agents or ingredients. Thus in further aspects, the invention encompasses pharmaceutical compositions for treating inflammatory diseases as defined above comprising a non-toxic therapeutically effective amount of a compound of the invention as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a diuretic; a sedating or non-sedating antihistamine. In addition the invention encompasses a method of treating inflammatory diseases comprising administration to a patient in need of such treatment a non-toxic therapeutically effect amount of a compound of the invention, optionally co-administered with one or more of such ingredients as listed immediately above.

The instant invention also involves a novel combination therapy comprising the administration of a therapeutically effective amount of an NSAID such as a COX-2 inhibitor in combination with a therapeutically effective amount of a compound of the invention to a mammal, and more particularly, to a human. The combination therapy is used to treat inflammatory diseases.

The instant pharmaceutical combinations comprising a compound of the invention in combination with an NSAID such as a COX-2 inhibitor include administration of a single pharmaceutical dosage formulation which contains both a compound of the invention and the NSAID, as well as administration of each active agent in its own separate pharmaceutical dosage formulation. Where separate dosage formulations are used, the compund of the invention and the NSAID can be administered at essentially the same time, i.e., concurrently, or at separately staggered times, i.e, sequentially. The "instant pharmaceutical combination" is understood to include all these regimens. Administration in these various ways are suitable for the present invention as long as the beneficial pharmaceutical effect of the compound of the invention and the NSAID are realized by the patient at substantially the same time. Such beneficial effect is preferably achieved when the target blood level concentrations of each active drug are maintained at substantially the same time. It is preferred that the compound of the invention and the NSAID be co-administered concurrently on a once-a-day dosing schedule; however, varying dosing schedules, such as the compound of the invention once per day and the NSAID once, twice or more times per day, or the NSAID once per day and the compound of the invention once, twice or more times per day, is also encompassed herein. A single oral dosage formulation comprised of both the compound of the invention and the NSAID is preferred. A single dosage formulation will provide convenience for the patient.

The instant invention also provides pharmaceutical compositions comprised of a therapeutically effective amount of an NSAID, or a pharmaceutically acceptable salt thereof, in combination with a therapeutically effective amount of a compound of the invention, or a pharmaceutically acceptable salt thereof, and a pharmaceutically acceptable carrier. One embodiment of the instant compositions is a single composition adapted for oral administration comprised of a therapeutically effective amount of a COX-2 inhibitor in combination with a therapeutically effective amount of a compound of the invention and a pharmaceutically acceptable carrier. The combination can also be administered in separate dosage forms, each having one of the active agents. If administered in separate dosage forms, the separate dosage forms are administered such that the beneficial effect of each active agent is realized by the patient at substantially the same time.

Common NSAIDs include salicylates such as aspirin, sodium salicylate, choline salicylate, salicylsalicylic acid, diflunisal, and salsalate; indoleacetic acids such as indomethacin and sulindac; pyrazoles such as phenylbutazone, oxyphenbutazone; pyrrolealkanoic acids such as tolmetin; phenylacetic acids such as ibuprofen, feroprofen, flurbiprofen, and ketoprofen; fenamates such as mefanamic acid, and meclofenamate; oxicams such as piroxicam; and naphthaleneacetic acids such as naproxen. Cyclo-oxygenase inhibitors such as COX-1 and COX-2 inhibitors are also NSAIDs.

Employing the human whole blood COX-1 assay and the human whole blood COX-2 assay described in C. Brideau et al, *Inflamm. Res.* 45: 68–74 (1996), herein incorporated by reference, preferably, the compounds have a cyclooxygenase-2 $IC_{50}$ of less than about 2 $\mu M$ in the human whole blood COX-2 assay, yet have a cyclooxygenase-1 $IC_{50}$ of greater than about 5 $\mu M$ in the human whole blood COX-1 assay. Also preferably, the compounds have a selectivity ratio of cyclooxygenase-2 inhibition over cyclooxygenase-1 inhibition of at least 10, and more preferably of at least 40. The resulting selectivity may indicate an ability to reduce the incidence of common NSAID-induced side effects.

The inhibitor of cyclooxygenase-2 may be administered at a dosage level up to conventional dosage levels for NSAIDs. Suitable dosage levels will depend upon the antiinflammatory effect of the chosen inhibitor of cyclooxygenase-2, but typically suitable levels will be about 0.001 to 50 mg/kg per day, preferably 0.005 to 30 mg/kg per day, and especially 0.05 to 10 mg/kg per day. The compound may be administered on a regimen of up to 6 times per day, preferably 1 to 4 times per day, and especially once per day.

The dosage regimen utilizing a compound of the invention in combination with the NSAID is selected in accordance with a variety of factors including type, species, age, weight, sex and medical condition of the patient; the severity of the condition to be treated; the route of administration; the renal and hepatic function of the patient; and the particular compound or salt or ester thereof employed. Since two different active agents are being used together in a combination therapy, the potency of each of the agents and the interactive effects achieved by combining them together must also be taken into account. A consideration of these factors is well within the purview of the ordinarily skilled clinician for the purpose of determining the therapeutically effective or prophylactically effective dosage amounts needed to prevent, counter, or arrest the progress of the condition.

Administration of the drug combination to the patient includes both self-administration and administration to the patient by another person.

Additional active agents may be used in combination with the compound of the invention in a single dosage formulation, or may be administered to the patient in a separate dosage formulation, which allows for concurrent or sequential administration. Examples of additional active agents which may be employed include HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors; probucol; niacin; fibrates such as clofibrate, fenofibrate, and gemfibrizol; cholesterol absorption inhibitors; bile acid sequestrants; LDL (low density lipoprotein) receptor inducers; vitamin $B_6$ (also known as pyridoxine) and the pharmaceutically acceptable salts thereof such as the HCl salt; vitamin $B_{12}$ (also known as cyanocobalamin); β-adrenergic receptor blockers; folic acid or a pharmaceutically acceptable salt or ester thereof such as the sodium salt and the methylglucamine salt; and antioxidant vitamins such as vitamin C and E and beta carotene.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including anti-hypercholesterolemics (e.g. HMG CoA reductase inhibitors such as lovastatin and simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

Compounds having the general structure

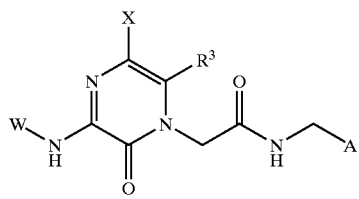

wherein W, X and $R^3$ have the above-described meanings and A is fluoropyridyl, can be prepared by reacting

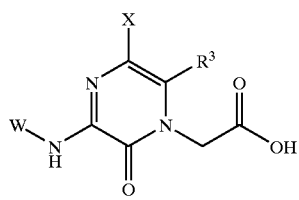

with

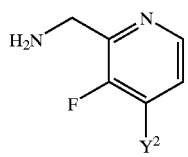

under conditions suitable for forming amide bond between the acid and the amine.

Suitable carboxylic acid starting materials for

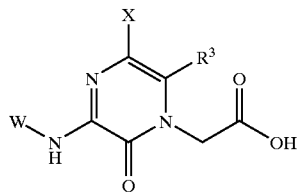

may be prepared according to the following procedures described in Sanderson et al., WO 97/40024, specifically Method 1 through step F and corresponding Example I, Method 2 and corresponding Example III, Method 3 through step E and corresponding Example V, and Method 5 through step E and corresponding Example LXXXII, on pages 29–58 and 108–111, the contents of which are hereby incorporated by reference. Alternatively, they may be prepared using ethyl 3-bromo-6-methylpyrazin-2-one-1-acetate (see Sanderson et al., WO 99/11267, compound 7-4, pages 34–37 the contents of which are hereby incorporated by reference, referenced as compound "A") in a condensation reaction with W—$NH_2$, followed by saponification which leads to the corresponding acid.

Compounds are then formed by reacting the carboxylic acid with

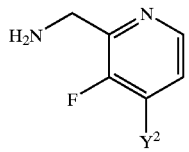

as shown below:

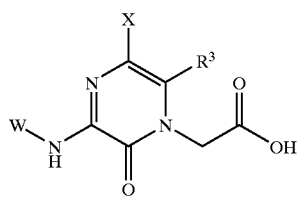

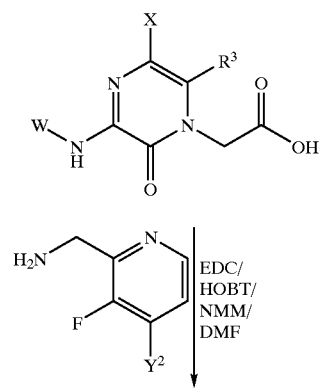

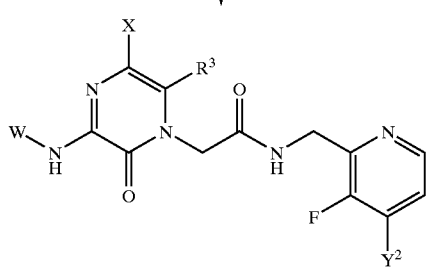

wherein

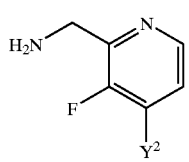

can be, for example, 2-aminomethyl-3-fluoropyridine (referenced as compound "B") and related fluoropyridine derivatives, in order to form the finished product. 2-aminomethyl-3-fluoropyridine is prepared as follows:

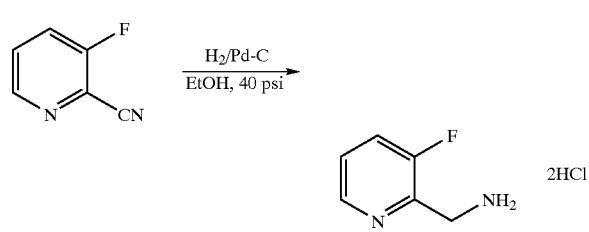

Synthesis of 2-aminomethyl-3-fluoropyridine begins with catalytic reduction of 2-cyano-3-fluoropyridine (Sakamoto et al., Chem. Pharm. Bull. 33(2) 565–571 (1985)) using palladium on carbon which provides 2-aminomethyl-3-fluoropyridine B as the dihydrochloride salt.

The coupling of 2-aminomethyl-3-fluoropyridine B and 3-(2,2-difluoro-2-(2-pyridyl)ethylamino)-6-methylpyrazin-2-one-1-acetic acid is carried out in DMF using EDC, HOBT and triethylamine. Addition of water precipitates the product which is then purified by silica gel chromatography to give the title compound as a slightly colored solid. Conversion to its hydrochloride salt can be carried out by treating an ethyl acetate solution with two equivalents of 1M HCl in ethyl acetate, followed by filtration.

2-Aminomethyl-3-fluoropyridine (B) as a Dihydrochloride Salt

A stirred solution of 6.11 g (50.1 mmol) of 2-cyano-3-fluoropyridine in 250 mL of ethanol and 12.5 mL (150 mmol) of conc. HCl was hydrogenated over 1.90 g of 10% palladium on carbon at 40 psi for 16 h. The catalyst was removed by filtration and the solvents removed at reduced pressure. The resulting solid was diluted with acetonitrile and filtered to give 8.0 g of the title compound as an off-white solid: $^1$H NMR (CD$_3$OD) δ 8.48 (d, 1H, 4.8 Hz), 7.69 (td, 1H, 9.2, 1.1 Hz), 7.68 (ddd, 1H, 8.8, 4.4, 4.4 Hz), 4.34 (s, 2 H).

Typically, solution phase amide couplings may be used to form the final product, but solid-phase synthesis by classical Merrifield techniques may be employed instead. The addition and removal of one or more protecting groups is also typical practice.

Compounds having different groups at variable A can be prepared by coupling alternative commercially available amino derivatives

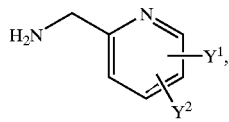

where $Y^1$ and $Y^2$ are defined above, using the coupling procedure described for coupling

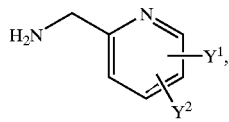

to the carboxylic acid. Alternative amino derivatives and methods for preparing amino derivatives are known to those skilled in the art and described below.

1)

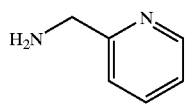

is commercially available.

2)

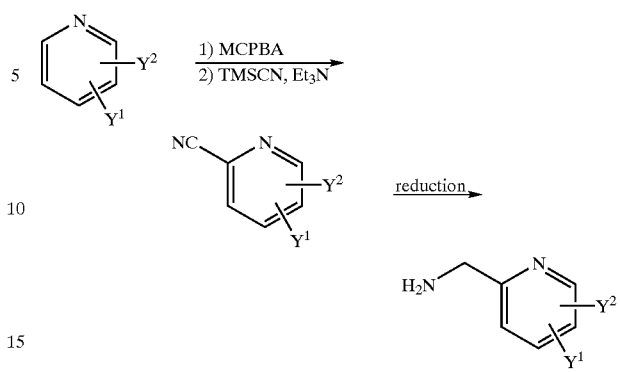

for example

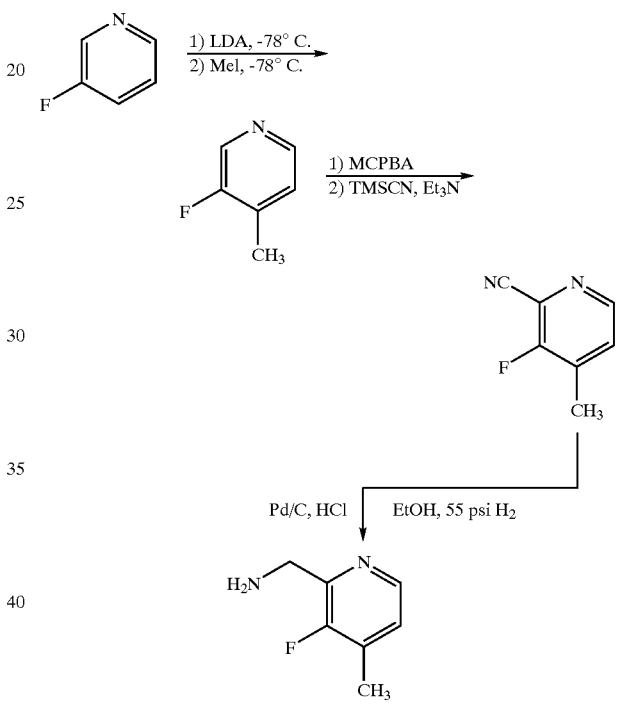

and also for example

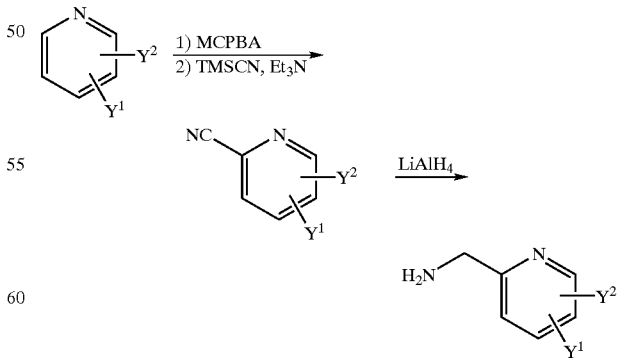

Unless otherwise stated, all NMR determinations were made using 400 MHz field strength.

EXAMPLE 1
3-Fluoro-2-pyridylmethyl-3-(2,2-difluoro-2-(2-pyridyl)ethylamino)-6-methylpyrazin-2-one-1-acetamide
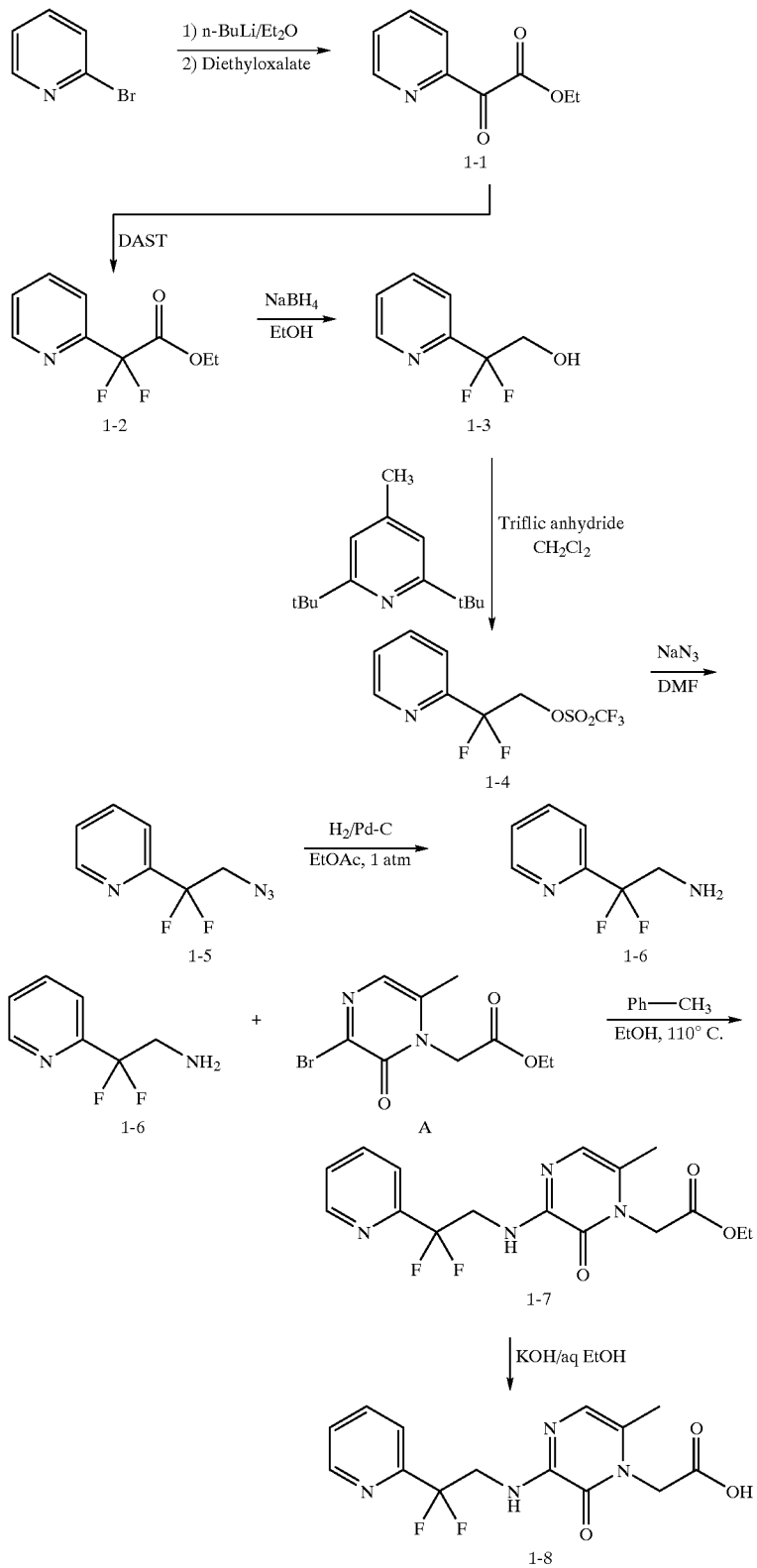

The synthesis of the 2,2-difluoro-2-(2-pyridyl)ethylamine 1-6-involves generation of 2-lithiopyridine from 2-bromopyridine in ether, followed by reaction with diethyl oxalate to give the 2-pyridylketoester 1-1. Treatment with excess diethylaminosulfurtrifluoride provides ethyl difluoro-2-pyridylacetate 1-2 which is reduced without purification using sodium borohydride. The resulting 2,2-difluoro-2-pyridylethanol 1-3 is purified by chromatography and converted to the corresponding triflate 1-4 using triflic anhydride and 2,6-di-t-butyl-4-methylpyridine as the base. The crude triflate is then treated with sodium azide in DMF to give 2,2-difluoro-2-pyridylethyl azide 1-5 which is also purified by silica gel chromatography. Reduction of the azide by catalytic hydrogenation provides the 2,2-difluoro-2-pyridylethylamine 1-6.

Condensation of this material with ethyl 3-bromo-6-methylpyrazin-2-one-1-acetate A in toluene/ethanol gives ethyl 3-(2,2-difluoro-2-(2-pyridyl)ethylamino)-6-methylpyrazin-2-one-1-acetate 1-7. Saponification of then provides the intermediate 3-(2,2-difluoro-2-(2-pyridyl)ethylamino)-6-methyl-pyrazin-2-one-1-acetic acid 1-8.

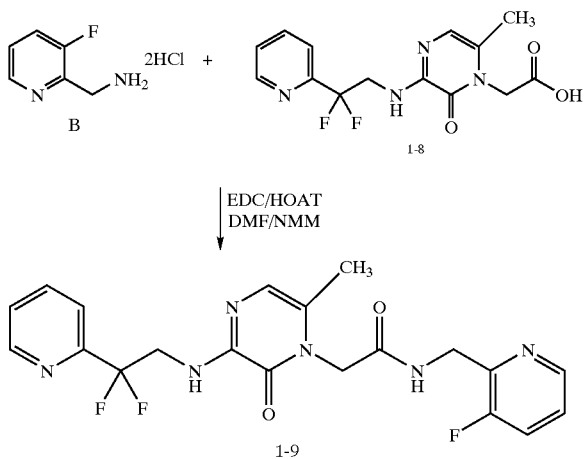

The coupling of 2-aminomethyl-3-fluoropyridine B and 3-(2,2-difluoro-2-(2-pyridyl)ethylamino)-6-methylpyrazin-2-one-1-acetic acid 1-8 is carried out in DMF using EDC, HOAT and N-methylmorpholine. Addition of water precipitates the product which is then purified by silica gel chromatography to give the title compound as a slightly colored solid. Conversion to its hydrochloride salt can be carried out by treating an ethyl acetate solution with two equivalents of 1M HCl in ethyl acetate, followed by filtration.

Ethyl 2-Pyridinoylformate (1-1).

To a stirred solution of 20 mL (210 mmol) of 2-bromopyridine in 500 mL of dry ether at −78° C. under Ar was added 85 mL of a 2.5 M solution of n-butyllithium in hexane in a slow stream. After stirring in the cold for 30 min, the solution was transferred over a 5 min period via two cannula into a 0° C. stirred solution of 100 mL (736 mmol) of diethyl oxalate in 1.0 L of dry ether under Ar. After stirring for 2 h in the cold, the reaction mixture was washed with 600 mL of sat. NaHCO$_3$, water, and brine. The solution was dried over MgSO$_4$ and the solvents concentrated at reduced pressure to give a red oil that was purified by SiO$_2$ chromatography (10×15 cm) using 1:4 to 35:65 EtOAc-hexanes. The product-containing fractions were concentrated at reduced pressure to afford 1-1 as a reddish oil: $^1$H NMR (CDCl$_3$) δ 1.42 (t, 3H), 4.45–4.55 (m, 2H), 7.55–7.6 (m, 1H), 7.9–7.95 (m, 1H), 8.11 (d, 1H), 8.78 (d, 1H).

Ethyl Difluoro-2-pyridylacetate (1-2).

A stirred solution of 22 g (123 mmol) of ethyl 2-pyridinoylformate 1-1 and 75 g (465 mmol) of diethylaminosulfurtrifluoride (DAST) were heated to 55° C. under Ar overnight. Because the reaction was not complete, 5 g additional DAST was added, and the reaction heated for an additional 24 h. The reaction mixture was cooled to rt, and poured very slowly into a stirred mixture of 1 kg of ice, 400 mL of ethyl acetate and 500 mL of sat. NaHCO$_3$. After the addition, the mixture was basified by the addition of solid NaHCO$_3$. The aqueous layer was extracted with EtOAc, and the combined organic layers washed with sat. NaHCO$_3$, brine, dried over Na$_2$SO$_4$ and the solvents concentrated at reduced pressure to give 1-2 as a brown oil: $^1$H NMR (CDCl$_3$) δ 1.35 (t, 3H), 4.35–4.4 (m, 2H), 7.4–7.45 (m, 1H), 7.75 (d, 1H), 7.95 (d, 1H), 8.45 (d, 1H).

2,2-Difluoro-2-(2-pyridyl)ethanol (1-3).

To a stirred solution of 19.5 g (97 mmol) of ethyl difluoro-2-pyridylacetate 1-2 in 200 mL of absolute ethanol at 0° C. was added 4.42 g (116 mmol) of sodium borohydride in small portions. After 30 min, the reaction was quenched by the addition of 50 mL of sat. NH$_4$Cl. The reaction mixture was concentrated at reduced pressure and the residue partitioned between 500 mL of ethyl acetate and sat. NaHCO$_3$. The organic layer was washed with water, brine, and dried over Na$_2$SO$_4$ and concentrated at reduced pressure to give a brown oil that was purified on SiO$_2$ (10×17 cm) using 1:1 EtOAc-hexane. After re-chromatographing the mixed fractions, all clean fractions were combined and concentrated at reduced pressure, giving 1-3 as a beige crystalline solid: $^1$H NMR (CDCl$_3$) δ 3.6 (t, 1H), 4.17–4.3 (m, 2H), 7.4–7.45 (m, 1H), 7.73 (d, 1H), 7.84–7.91 (m, 1H), 8.61 (d, 1H).

2,2-Difluoro-2-(2-pyridyl)ethyl Trifluoromethanesulfonate (1-4).

To a stirred solution of 5 g (31.4 mmol) of 2,2-difluoro-2-(2-pyridyl)ethanol 1-3 and 9.69 g (47.2 mmol) of 2,6-di-t-butyl-4-methylpyridine in 110 mL of methylene chloride at −78° C. under Ar was added 7.93 mL (47.2 mmol) of triflic anhydride dropwise. After 1 h, the reaction was diluted with 100 mL of pentane and filtered. The filtrate was concentrated and treated again with pentane and filtered. Concentration of the filtrate gave 1-4 as a brown oil, contaminated with 2,6-di-t-butyl-4-methylpyridine: $^1$H NMR (CDCl$_3$) δ 5.12 (t, 2H), 7.45–7.5 (m, 1H), 7.75 (d, 1H), 7.86–7.94 (m, 1H), 8.65 (d, 1H).

2,2-Difluoro-2-(2-pyridyl)ethylazide (1-5).

To a stirred solution of 5.5 g of 2,2-difluoro-2-(2-pyridyl) ethyl trifluoromethanesulfonate 1-4 in 70 mL of DMF was added 6.74 g (104 mmol) of sodium azide under Ar. The mixture was heated to 60° C. overnight. A second batch was run in the same manner, and after cooling to rt, both reactions were poured into 600 mL of water, and extracted with 3×500 mL of ether. The combined extracts were washed with brine, dried over Na$_2$SO$_4$ and concentrated at reduced pressure to give an oil that was purified by SiO$_2$ (10×6 cm) using hexane 1:3 EtOAc-hexane and 1:1 EtOAc-hexane. The product-containing fractions were concentrated at reduced pressure to give 1-5 as a yellow oil: $^1$H NMR (CDCl$_3$) δ 4.05 (t, 2H), 7.4–7.45 (m, 1H), 7.73 (d, 1H), 7.83–7.89 (m, 1H), 8.67 (d, 1H).

2,2-Difluoro-2-(2-pyridyl)ethylamine (1-6).

A stirred solution of 100 mg of 2,2-difluoro-2-(2-pyridyl) ethylazide 1-6 was hydrogenated in 10 mL of ethyl acetate over 100 mg of 10% palladium on carbon using a balloon for 1 h. The catalyst was removed by filtration and the solvents removed at reduced pressure. A total of 1.8 g (9.7 mmol) of the azide was reduced using this procedure to give 1-6 as a yellow oil: ¹H NMR (CDCl₃) δ 8.66 (d, 1H, 4.2 Hz), 7.82 (td, 1H, 7.7, 1.7 Hz), 7.68 (d, 1H, 8.1 Hz), 7.37–7.40 (m, 1H), 3.44 (t, 2 H, 14.3 Hz), 1.41 (br s, 2H).

Ethyl 3-(2,2-Difluoro-2-(2-pyridylethylamino)-6-methylpyrazin(1H)-2-one-1-acetate (1-7).

A solution of 7.13 g (45.1 mmol) of 2,2-difluoro-2-(2-pyridyl)ethylamine and 12.4 g (45.1 mmol) of ethyl 3-bromo-6-methylpyrazin(1H)-2-one-1-acetate was heated to 125° C. in a sealed tube overnight in 15 mL of toluene and 15 mL of ethanol. The reaction was concentrated and the residue was diluted with ethyl acetate, washed with 15% NaHCO₃ and the aqueous layer backwashed with 3 portions of ethyl acetate. The combined organic layers were dried over MgSO₄ and the solvents removed at reduced pressure to give an oil that was chromatographed on SiO₂ using 50:50 hexane-EtOAc to give the title compound as a pale yellow solid: ¹H NMR (CDCl₃) δ 8.67 (d, 1H, 4.8 Hz), 7.80 (t, 1H, 7.9 Hz), 7.68 (d, 1H, 7.9 Hz), 7.36–7.39 (m, 1H), 6.71 (s, 1H), 6.31 (br t, 1H), 4.69 (s, 2H), 4.35 (td, 2H, 14.1, 6.6 Hz), 4.24 (q, 2H, 7.1 Hz), 2.11 (s, 3H), 1.29 (t, 3 H, 6.8 Hz).

3-(2,2-Difluoro-2-(2-pyridylethylamino)-6-methylpyrazin(1H)-2-one-1-acetic Acid (1-8).

To a stirred solution of 9.67 g (27.5 mmol) of ethyl 3-(2,2-difluoro-2-(2-pyridylethylamino)-6-methylpyrazin(1H)-2-one-1-acetate in 100 mL of methanol was added 8.58 g (153.0 mmol) of potassium hydroxide in 20 mL of water. After 1 h, the solution was concentrated at reduced pressure, and the residue dissolved in 25 mL of water. This solution was acidified to pH=7 using 1.3 M HCl, and concentrated at reduced pressure to give a yellow solid containing potassium chloride and the title compound: ¹H NMR (CD₃OD) δ 8.65 (d, 1H, 4.7 Hz), 7.95 (td, 1H, 7.9, 1.8 Hz), 7.72–7.74 (m, 1H), 7.50–7.54 (m, 1H), 6.64 (d, 1H, 1.09 Hz), 4.78 (s, 2H), 4.31 (t, 2H, 14.1 Hz), 2.16 (s, 3H).

3-Fluoro-2-pyridylmethyl-3-(2,2-difluoro-2-(2-pyridyl)ethylamino)-6-methylpyrazin-2-one-1-acetamide (1-9).

A stirred solution of 300.1 g (0.418 mmol) of 3-(2,2-difluoro-2-(2-pyridylethylamino)-6-methylpyrazin(1H)-2-one-1-acetic acid 1-8 and 99 mg (0.501 mmol) 2-aminomethyl-3-fluoropyridine B dihydrochloride in 3 mL of DMF was added 50.0 mg (0.26 mmol) of EDC, 35.0 mg (0.26 mmol) of HOBT and 304 mg (3.0 mmol) of triethylamine. After stirring for 1 d, the volatiles were removed at reduced pressure. The resulting dark oil was diluted with ethyl acetate, washed with 5% NaHCO₃ and the aqueous layer backwashed with 3 portions of ethyl acetate. The combined organic layers were dried over MgSO₄ and the solvents removed at reduced pressure to give an oil that was chromatographed on SiO₂ using 95:5 chloroform-MeOH to give the title compound as a pale yellow solid: ¹H NMR (CDCl₃) δ 8.67 (dd, 1H, 0.7, 4.8 Hz), 8.31 (ddd, 1H, 1.3, 1.3, 4.6 Hz), 7.81 (ddd, 1H, 1.7, 7.7, 7.7 Hz), 7.69 (ddd, 1H, 0.9, 0.9, 8.1 Hz), 7.20 (br t, 1H), 7.37 (m, 2H), 7.23 (ddd, 1H, 8.6, 4.3, 4.3 Hz), 6.75 (d, 1H, 0.9 Hz), 6.34 (br t, 1H, 6.3 Hz), 4.73 (s, 2H), 4.63 (dd, 2H, 4.7, 1.6 Hz), 4.37 (td, 2H, 14.2, 6.5 Hz), 2.25 (d, 3H, 0.9 Hz Conversion to the dihydrochloride salt can be carried out by treating a dioxane solution with two equivalents of 4.0 M HCl in dioxane, followed by concentration: ¹H NMR (CD₃OD) δ 8.71 (br d, 1H, 4.6 Hz), 8.56 (dd, 1H, 0.9, 5.3 Hz), 8.15 (ddd, 1H, 0.9, 8.9, 8.9 Hz), 8.05 (ddd, 1H, 1.6, 7.8, 7.8 Hz), 7.83 (d, 1H, 8.1 Hz), 7.81 (m, 1H), 7.61 (dd, 1H, 5.1, 7.3 Hz), 6.68 (d, 1H, 0.9 Hz), 4.88 (s, 2H), 4.74 (d, 2H, 1.3 Hz), 4.44 (t, 2H, 14.4 Hz), 2.25 (d, 3H, 0.8 Hz).

EXAMPLE 2

Following the synthesis described below, a chloropyrazinone derivative of compound 1-9 was prepared.

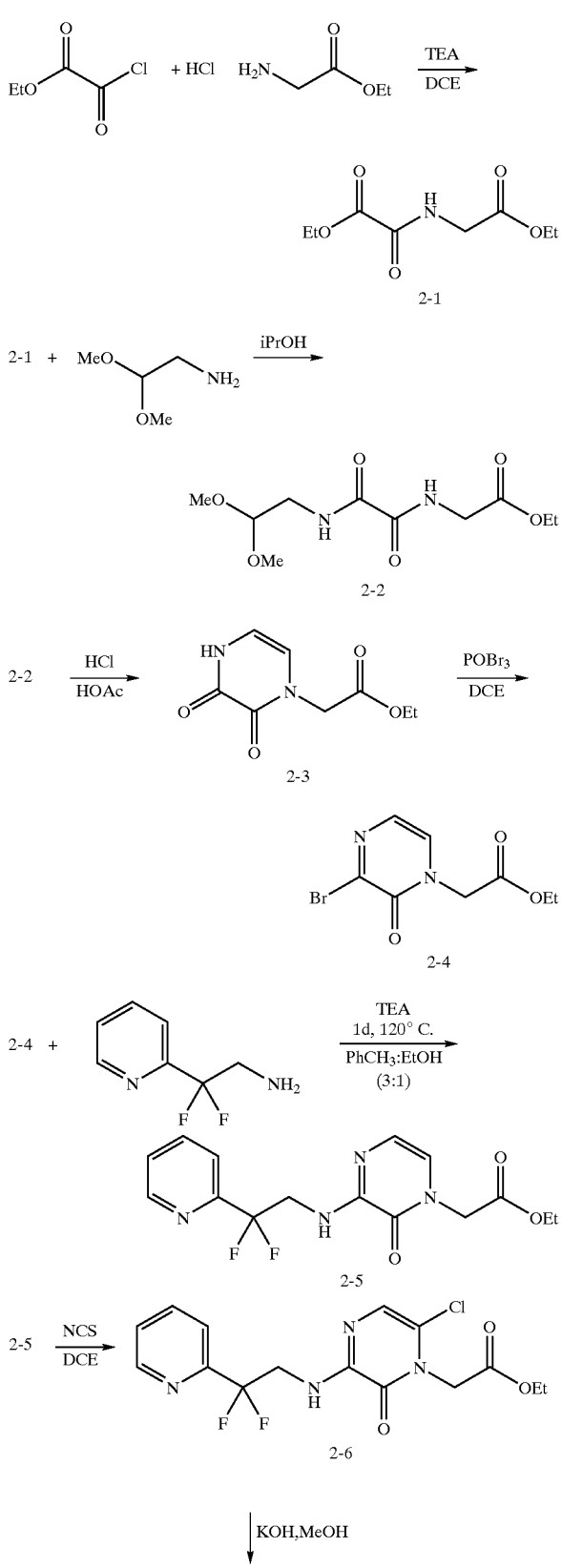

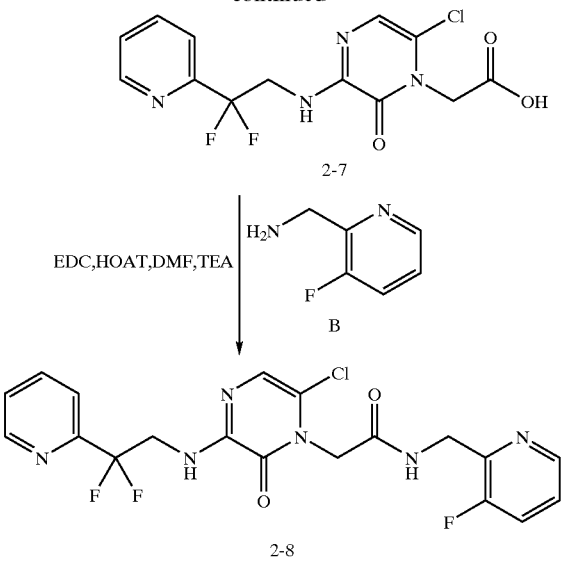

Ethyl N-(Ethylcarboxymethyl)oxamate (2-1)

To a suspension of ethyl glycine·HCl (38.4 g, 275 mmol) in 1,2-dichloroethane (360 mL) was added triethylamine (77.0 mL, 550 mmol) at room temperature. After stirring for 30 minutes the heterogenous mixture was cooled to 0° C. and ethyl oxalyl chloride (30.3 mL, 275 mol) was added dropwise over the course of 1 h. Upon completion of the addition, the cooling bath was removed and the reaction was stirred at room temperature overnight. The reaction was diluted with water (250 mL) and the layers separated. The aqueous layer was backwashed with 2 portions of dichloromethane (250 mL). The combined organic layers were washed with water (250 mL), followed by brine (250 mL), dried over $MgSO_4$ and concentrated to give an oil 2-1 that was taken directly onto the next step.

N-(Ethylcarboxymethyl)-N'-(2,2-dimethoxyethyl)oxamide (2-2)

To a solution of the oxamate (84.0 g, 414 mmol) 2-1 in 2-propanol (500 mL) was added aminoacetaldehyde dimethyl acetal (45.7 g, 435 mmol) in one portion. After stirring overnight at room temperature, the reaction mixture was concentrated to a thick orange oil. This thick slurry was diluted with 2-propanol (300 mL) and the solid was broken up with a spatula. Filtration afforded a solid which was further rinsed with an additional portion of 2-propanol. Removal of residual 2-propanol was accomplished via high vacuum to afford a light orange solid 2-2. (89.8 g): $^1$H NMR (CDCl$_3$) δ 7.82 (br s, 1H), 7.50 (br s, 1H), 4.41 (t, 1H, 5.3 Hz), 4.24 (q, 2H, 7.1 Hz), 4.09 (d, 2H, 5.9 Hz), 3.47 (dd, 2H, 5.3, 6.2 Hz), 3.40 (s, 6H), 1.30 (t, 3H, 7.1 Hz).

Ethyl 3-Hydroxypyrazin(1H)-2-one-1-acetate (2-3)

A solution of the oxamide (89.8 g, 343 mmol) 2-2, acetic acid (400 mL), and conc. HCl (2 mL) was heated to reflux. After 1 h the black reaction was concentrated to a thick oil (high vacuum employed to ensure complete removal of AcOH) which was diluted with EtOH (150 mL) and MeOH (150 mL). Scraping the thick black oil with a spatula induced precipitation of the product. The MeOH was removed via rotary evaporation and the remaining slurry was filtered and rinsed with EtOH (200 mL) to deliver a tan solid. Recrystallization from refluxing EtOH (300 mL) afforded an off-white powder 2-3: $^1$H NMR (CD$_3$OD) δ 6.50 (d, 1H, 5.9 Hz), 6.36 (d, 1H, 5.9 Hz), 4.58 (s, 2H), 4.23 (q, 2H, 7.1 Hz), 1.28 (t, 3H, 7.1 Hz). Further crude dione could be obtained upon concentration of the mother liquor.

Ethyl 3-Bromopyrazin(1H)-2-one-1-acetate (2-4) A solution of the hydroxypyrazinone (25.0 g, 126 mmol) 2-3 and phosphorous oxybromide (37.9 g, 132 mmol) in 1,2-dichloroethane (250 mL) was heated to reflux. After 8 h the reaction mixture was treated with sat. aq. Na$_2$CO$_3$ (250 mL) and stirred for 1 h. The mixture was diluted with water (100 mL) and dichloromethane (100 mL), the layers were separated and the aqueous layer was backwashed with EtOAc (3×200 mL). The combined organics were dried (MgSO$_4$), and concentrated to give an oil which was stored on a high vacuum line overnite to afford brown solid 2-4: $^1$H NMR (CDCl$_3$) δ 7.17 (d, 1H, 4.2 Hz), 7.07 (d, 1H, 4.2 Hz), 4.65 (s, 2H), 4.27 (q, 2H, 7.2 Hz), 1.31 (t, 3H, 7.2 Hz).

Ethyl 3-(2,2-Difluoro-2-(2-pyridylethylamino)pyrazin(1H)-2-one-1-acetate (2-5)

A solution of 4.80 g (30.4 mmol) of 2,2-difluoro-2-(2-pyridyl)ethylamine, 4.24 mL (30.4 mmol) of triethylamine and 7.93 g (30.4 mmol) of ethyl 3-bromopyrazin(1H)-2-one-1-acetate 2-4 was heated to 120° C. in a sealed tube overnight in 12 mL of toluene and 4 mL of ethanol. The reaction was concentrated and the residue was partitioned between dichloromethane and sat. aq. NaHCO$_3$. The aqueous layer was backwashed with 4 portions of dichloromethane. The combined organic layers were dried over MgSO$_4$ and the solvents removed at reduced pressure to give an oil that was chromatographed on SiO$_2$ using 60:40 to 40:60 hexane-EtOAc to give 2-5 as a yellow solid: $^1$H NMR (CDCl$_3$) δ 8.67 (dd, 1H, 4.8, 0.7 Hz), 7.81 (ddd, 1H, 7.8, 7.8, 1.7 Hz), 7.69 (dd, 1H, 7.8, 1 Hz), 7.38 (dd, 1H, 5.1, 7.0 Hz), 6.86 (d, 1H, 4.8 Hz), 6.54 (br t, 1H, 5.9 Hz), 6.40 (d, 1H, 4.6 Hz), 4.54 (s, 2H), 4.38 (td, 2H, 14.0, 6.4 Hz), 4.24 (q, 2H, 7.1 Hz), 1.29 (t, 3H, 7.1 Hz).

Ethyl 3-(2,2-Difluoro-2-(2-pyridylethylamino)-6-chloropyrazin(1H)-2-one-1-acetate (2-6)

To a stirred solution of 6.81 g (20.1 mmol) of ethyl 3-(2,2-difluoro-2-(2-pyridylethylamino)pyrazin(1H)-2-one-1-acetate 2-5 and 2.42 g (18.1 mmol) of N-chlorosuccinimide in 100 mL of 1,2-dichloroethane was heated to reflux. An additional 242 mg (1.81 mmol) and 75 mg (0.56 mmol) of NCS were added to the reaction mixture after 1 h and 1.5 h, respectively. After 2.5 h total, the solution was cooled to room temperature and partitioned between dichloromethane (150 mL) and sat. aq. NaHCO$_3$ (200 mL). The layers were separated and the aqueous phase was backwashed with dichloromethane (2×200 mL). The combined organic layers were dried over MgSO$_4$ and the solution concentrated to a volume of 10 mL. This liquid was directly loaded onto a SiO$_2$ column and eluted with 65:35 to 55:45 hexane-EtOAc to give 2-6 as a yellow solid: $^1$H NMR (CDCl$_3$) δ 8.68 (d, 1H, 4.8, Hz), 7.83 (ddd, 1H, 7.7, 7.7, 1.6 Hz), 7.9 (dd, 1H, 7.9 Hz), 7.40 (dd, 1H, 4.9, 7.3 Hz), 6.96 (s, 1H), 6.49 (br t, 1H, 5.9 Hz), 4.89 (s, 2H), 4.38 (td, 2H, 13.9, 6.5 Hz), 4.26 (q, 2H, 7.1 Hz) (t, 3H, 7.1 Hz).

3-(2,2-Difluoro-2-(2-pyridylethylamino)-6-chloropyrazin(1H)-2-one-1-acetic Acid (2-7)

To a stirred solution of 7.27 g (19.5 mmol) of ethyl 3-(2,2-difluoro-2-(2-pyridylethylamino)-6-chloropyrazin (1H)-2-one-1-acetate 2-6 in 200 mL of methanol was added 39 mL (39.0 mmol) of 1M aq. potassium hydroxide. After 3 h the solution was acidified to pH=7 using conc. HCl, and concentrated at reduced pressure (azeotrope with PhCH$_3$) to give a white solid containing potassium chloride and 2-7: $^1$H NMR (CD$_3$OD) δ 8.64 (d, 1H, 4.8 Hz), 7.93 (ddd, 1H, 7.7, 7.7, 1.5 Hz), 7.70 (d, 1H, 8.0 Hz), 7.49 (dd, 1H, 5.2, 7.4 Hz), 6.80 (s, 1H), 4.67 (s, 2H), 4.27 (t, 2H, 13.9 Hz).

3-Fluoro-2-pyridylmethyl-3-(2,2-difluoro-2-(2-pyridyl)ethylamino)-6-chloropyrazin-2-one-1-acetamide (2-8)

A stirred solution of 330 mg (0.536 mmol) of 3-(2,2-difluoro-2-(2-pyridylethylamino)-6-chloropyrazin(1H)-2-one-1-acetic acid 2-7 and 160 mg (0.805 mmol) 2-aminomethyl-3-fluoropyridine dihydrochloride in 2 mL of DMF was added 128 mg (0.67 mmol) of EDC, 91 mg (0.67 mmol) of HOAT and 0.30 mL (2.1 mmol) triethylamine. After stirring overnite, 80 mg of 2-aminomethyl-3-fluoropyridine dihydrochloride, 128 mg of EDC, 91 mg of HOAT and 0.08 mL (2.1 mmol) triethylamine were added. The reaction was stirred for an additional 24 h and the volatiles were removed en vacuo. The residue was diluted with sat. aq. NaHCO$_3$ (10 mL) and water (15 mL) and filtered to afford a tan solid. This material was chromatographed on SiO$_2$ using 1:99 to 5:95 MeOH-CH$_2$Cl$_2$ to give a yellow solid 2-8: $^1$H NMR (CDCl$_3$) δ 8.67 (d, 1H, 4.6 Hz), 8.32 (d, 1H, 4.6 Hz), 7.81 (dd, 1H, 7.8, 6.4 Hz), 7.69 (d, 1H, 7.8 Hz), 7.41–7.37 (m, 2H), 7.27–7.22 (m, 2H), 6.97 (s, 1H br t, 1H, 6.0 Hz), 4.93 (s, 2H), 4.66 (d, 2H, 4.0 Hz), 4.38 (td, 2H, 13.9, 6.5 Hz). 2-8 is also named 2-{3-[(2,2-difluoro-2-(2-pyridyl)ethyl)amino]-6-chloro-2-oxohydropyrazinyl}-N-{(3-fluoro(2-pyridyl))methyl]-acetamide. Conversion to the hydrochloride salt can be carried out by diluting the product with ethyl acetate (2 mL) and treating with 5 mL of 1.5M HCl in ethyl acetate, followed by filtration: $^1$H NMR (CD$_3$OD) δ 8.72 (d, 1H, 4.6 Hz), 8.56 (dd, 1H, 0.9, 5.3 Hz), 8.16–8.11 (m, 2H), 7.87 (d, 1H, 8.1 Hz), 7.80 (ddd, 1H, 4.8, 4.8, 9.0 Hz), 7.68 (dd, 1H, 5.4, 7.2 Hz), 6.87 (s, 1H), 4.95 (s, 2H), 4.74 (d, 2H, 1.1 Hz), 4.35 (t, 2H, 13.8 Hz).

EXAMPLE 3

Following the synthesis described below, thio-, sulfonyl and sulfinyl derivatives of compound 2–7 were prepared.

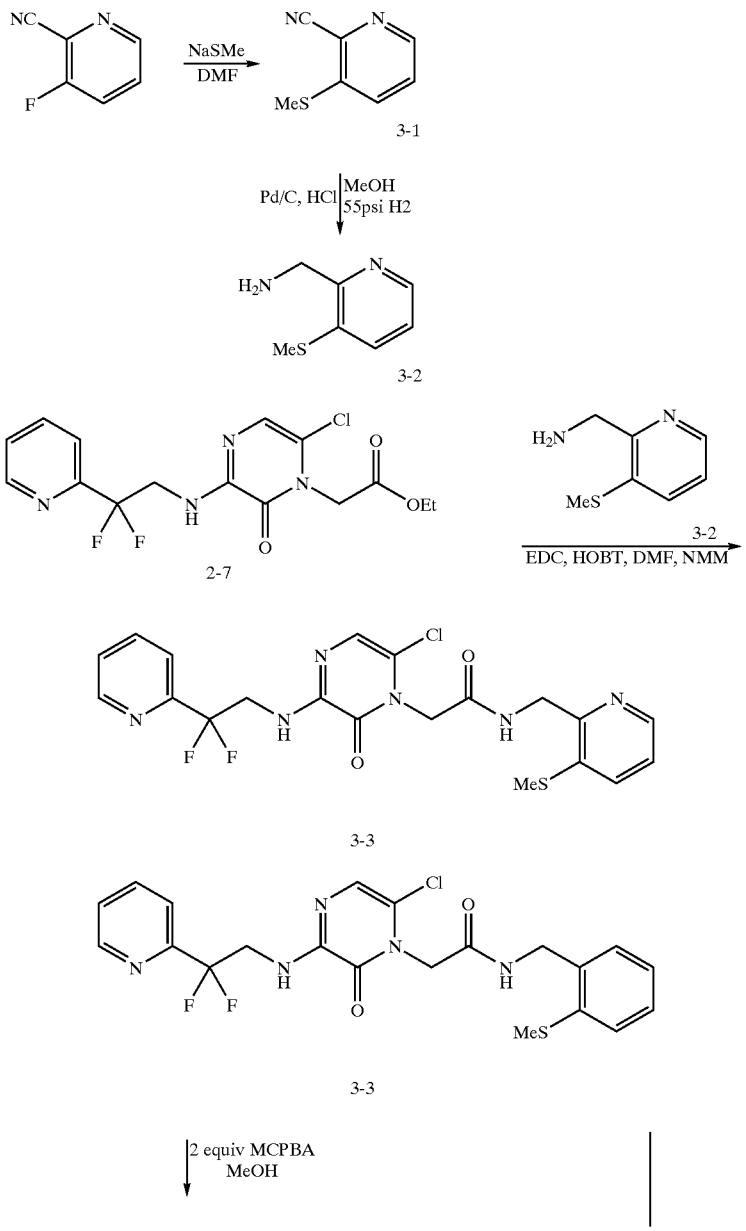

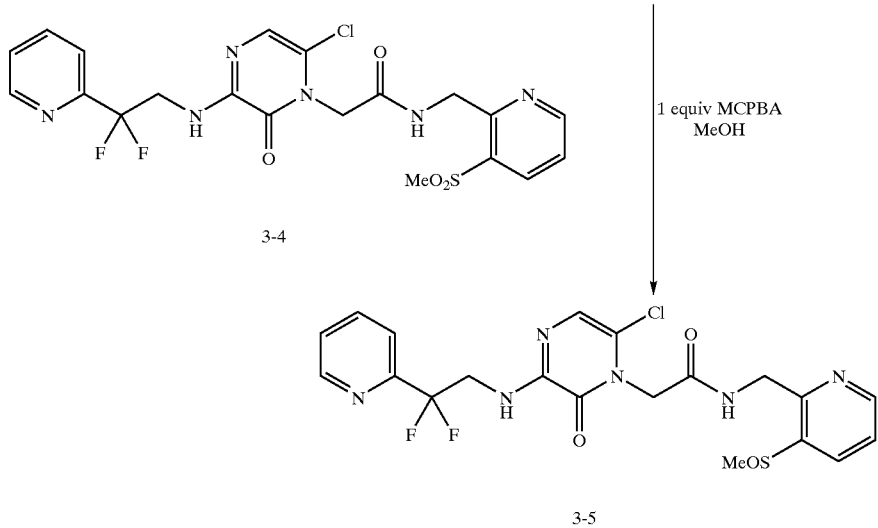

2-Cyano-3-methylthiopyridine (3-1)

A stirred solution of 1.00 g (8.19 mmol) of 2-cyano-3-fluoropyridine and 0.631g (9.01 mmol) of sodium thiomethoxide in 8 mL of DMF was stirred at room temperature for 1 h. The reaction mixture was diluted with water (80 mL) and stirred for 5 min. The resulting solid was filtered and dried on a high vacuum line to give 3-1 as an off-white solid: $^1$H NMR (CDCl$_3$) δ 8.46 (d, 1H, 4.6 Hz), 7.66 (d, 1H, 8.3 Hz), 7.44 (dd, 1H, 4.6, 8.3 Hz), 2.58 (s, 3H).

2-Aminomethyl-3-methylthiopyridine Dihydrochloride (3-2)

A stirred solution of 659 mg (4.39 mmol) of 2-cyano-3-methylthiopyridine 3-1 in 25 mL of methanol and 5 mL of 6M aq. HCl was hydrogenated over 659 mg of 10% palladium on carbon at 55 psi for 5 h. The catalyst was removed by filtration and the solvents concentrated at reduced pressure. The resulting material was diluted with methanol and concentrated (2x) to give 3-2 as an off-white solid: 1H NMR (CD$_3$OD): δ 2.58 (s, 3H), 4.28 (s, 2H), 7.43 (m, 1H), 7.86 (dd, J 1.3 and 8.1 Hz, 1H), 8.43 (dd, J=1.3 and 4.8 Hz, 1H).

3-Methylthio-2-pyridylmethyl-3-(2,2-difluoro-2-(2-pyridyl)ethylamino)-6-chloropyrazin-2-one-1-acetamide (3-3)

A stirred solution of 545 mg (0.886 mmol) of 3-(2,2-difluoro-2-(2-pyridylethylamino)-6-chloropyrazin(1H)-2-one-1 -acetic acid 2-7 and 144 mg (0.930 mmol) 2-aminomethyl-3-methylthiopyridine dihydrochloride 3-2 in 9 mL of DMF was added 178 mg (0.930 mmol) of EDC, 126 mg (0.930 mmol) of HOBT and 179 mg (1.77 mmol) NMM. After stirring overnite, the reaction was partitioned between EtOAc and 10% aqueous NaHCO$_3$ and an insoluble material was filtered off. The organic phase was washed with water, brine, dried (MgSO$_4$) and concentrated. This residue and the filtered solid were combined and chromatographed on SiO$_2$ using 1:99 to 5:95 MeOH-CHCl$_3$. This material was dissolved in 5 mL of methanol and 3 drops of HCl sat. ethanol were added. Concentration afforded 3-3 as a light yellow solid: $^1$H NMR (D$_6$ DMSO): δ 2.49 (obscured s, 3H), 4.22 (m, 2H), 4.42 (d, J=4.9 Hz, 2H), 4.82 (s, 2H), 6.91 (s, 1H), 7.34 (m, 2H), 7.57 (m, 1H), 7.70 (m, 2H), 7.96 (m, 1H), 8.32 (d, J=3.9 Hz, 1H), 8.69 (m, 2 H); HRMS (FAB) calcd C$_{20}$H$_{20}$ClF$_2$N$_6$O$_2$S (M+1) 481.1019, found 481.0999.

3-Methylsulfonyl-2-pyridylmethyl-3-(2,2-difluoro-2-(2-pyridyl)ethylamino)-6-chloropyrazin-2-one-1-acetamide (3-4)

3-Methylthio-2-pyridylmethyl-3-(2,2-difluoro-2-(2-pyridyl)ethylamino)-6-chloropyrazin-2-one-1-acetamide (15 mg, 0.031 mmol) 3-3 was suspended in 2.5 mL of methanol and treated with MCPBA (50–60%, 21.5 mg, 0.062 mmol). After stirring for 3 h, an additional equivalent of MCPBA (50–60%, 10.75 mg, 0.031 mmol) was added. The reaction was stirred overnight and sat. aq. NaHCO$_3$ was added until the solution was neutral. This mixture was concentrated and the residue was partitioned between EtOAc and water. The organic phase was washed with water, brine, dried (MgSO$_4$) and concentrated. This material was chromatographed on SiO$_2$ using 1:99 to 3:97 MeOH-CHCl$_3$ to afford 3-4: $^1$H NMR (CDCl$_3$): δ 3.25 (s, 3H), 4.38 (m, 2H), 4.91 (s, 2H), 4.96 (d, J=5.3 Hz, 2H), 6.50 (t, 1H), 6.98 (s, 1H), 7.26 (obscured m, 1H), 7.45 (m, 2H), 7.70 (dd, 1H), 7.84 (t, 1H), 8.32 (d, 1H), 8.67 (m, 2H), 8.47 (t, 1H); HRMS (FAB) calcd C$_{20}$H$_{20}$ClF$_2$N$_6$O$_4$S (M+1) 513.0923, found 513.0895.

[R,S] 3-Methylsulfinyl-2-pyridylmethyl-3-(2,2-difluoro-2-(2-pyridyl)ethylamino)-6-chloropyrazin-2-one-1-acetamide (3-5)

3-Methylthio-2-pyridylmethyl-3-(2,2-difluoro-2-(2-pyridyl)ethylamino)-6-chloropyrazin-2-one-1-acetamide (50 mg, 0.104 mmol) 3-3 was suspended in 8 mL of methanol and treated with MCPBA (50–60%, 35.9 mg, 0.104 mmol). After stirring for 1 h, sat. aq. NaHCO$_3$ was added until the solution was neutral. This mixture was then purified by HPLC to afford 3-5 as a colorless solid: $^1$H NMR (D$_6$ DMSO): δ 2.76 (s, 3H), 4.21 (m, 2H), 4.45 (m, 2H), 4.76 (s, 2H), 6.90 (s, 1H), 7.36. (m, 1H), 7.55 (m, 1H), 7.61 (m, 1H), 7.69 (d, 1H), 7.96 (t, 1H), 8.25 (d, 1H), 8.69 (m, 2H), 8.96 (t, 1H); HRMS (FAB) calcd C$_{20}$H$_{20}$ClF$_2$N$_6$O$_3$S (M+1) 497.0969, found 497.0970. The enantiomers were separated on a Chiralpak AD column, eluting with 1:1 2-propanol:hexanes/0.1% diethylamine (to afford the faster eluting enantiomer as a colorless solid) followed by 7:3 2-propanol:hexanes/0.1% diethylamine (to afford the slower eluting enantiomer as a colorless solid).

EXAMPLE 4

Preparation of 3-Fluoro-2-pyridylmethyl 3-(2,2-difluoro-2-(2-pyridyl)ethylamino)-6-cyanopyrazin-2-one-1-acetamide Hydrochloride (4-7)

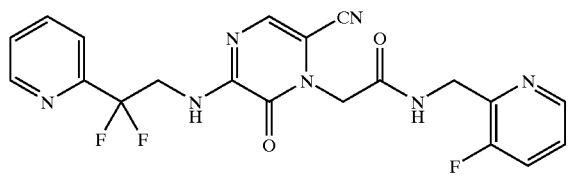

4-7

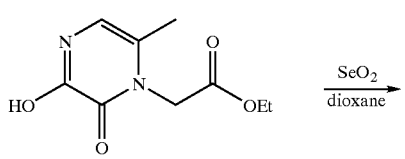

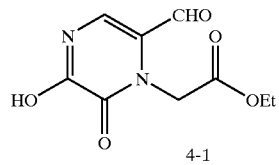

4-1

Step A: Ethyl 6-Formyl-3-hydroxypyrazin(1H)-2-one-1-acetate (4-1)

A suspension of the hydroxypyrazinone (5.0 g, 23.6 mmol) and selenium(IV) oxide (2.62 g, 23.6 mmol), in 1,4-dioxane (100 mL) was heated to reflux for 24 h. The dark reaction mixture was cooled and filtered through a pad of Celite with MeOH. Concentration and purification of the residue on a $SiO_2$ column with 3:97 to 10:90 $MeOH:CH_2Cl_2$ afforded 4-1 as an orange solid: $^1H$ NMR ($CD_3OD$) δ 9.11 (s, 1H), 7.39 (s, 1H), 5.12 (s, 2H), 4.22 (q, 2H, 7.1 Hz), 1.29 (t, 3H, 7.1 Hz).

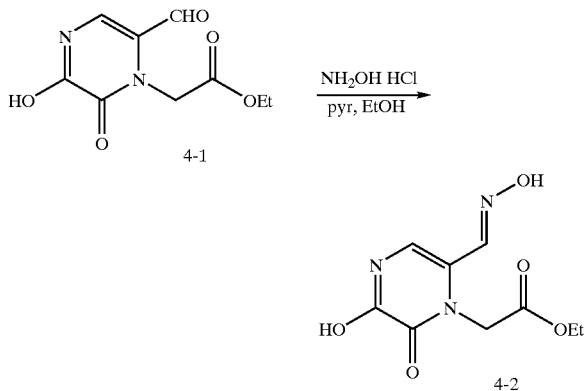

Step B: Ethyl 6-Formoximyl-3-hydroxypyrazin(1H)-2-one-1-acetate (4-2)

To a suspension of the formylpyrazinone 4-1 (5.43 g, 24.0 mmol) and hydroxylamine hydrochloride (1.67 g, 24.0 mmol) in ethanol (100 mL) was added pyridine (1.90 mL, 24.0 mmol). After 2 h at reflux, the reaction mixture was cooled and concentrated. This crude solid was recrystallized from ethanol (100 mL) to deliver 4-2 as a solid. Additional product was obtained by concentration of the filtrate and trituration with water (50 mL): $^1H$ NMR (DMSO) δ 11.85 (d, 1H), 11.19 (s, 1H), 7.82 (s, 1H), 6.79 (d, 1H, 5.9 Hz), 5.05 (s, 2H), 4.12 (q, 2H, 7.1 Hz), 1.20 (t, 3H, 7.1 Hz).

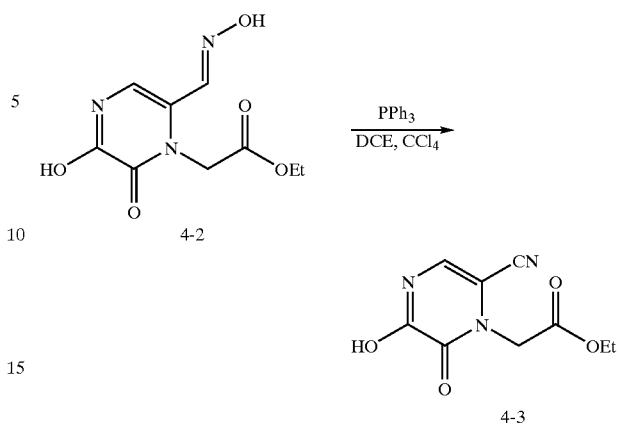

Step C: Ethyl 6-Cyano-3-hydroxypyrazin(1H)-2-one-1-acetate (4-3)

A slurry of the hydroxypyrazinone 4-2 (2.70 g, 11.2 mmol) and polymer-bound triphenylphosphine (1.55 mmol/g resin: 15.1 g, 23.5 mmol) in 1,2-dichloroethane (90 mL) and carbon tetrachloride (9 mL) was heated to reflux for 1.5 h. The reaction mixture was cooled, filtered, and the resin rinsed with of 1:1 $MeOH:CH_2Cl_2$ (200 mL). Concentration of the filtrate yielded 4-3 as a tan solid: $^1H$ NMR ($CDCl_3$) δ 7.06 (s, 1H), 4.73 (s, 2H), 4.29 (q, 2H, 7.1 Hz), 1.33 (t, 3H, 7.1 Hz).

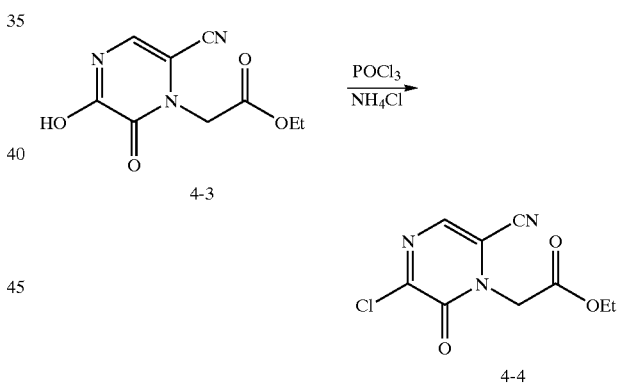

Step D: Ethyl 3-Chloro-6-cyanopyrazin(1H)-2-one-1-acetate (4-4)

A suspension of the hydroxypyrazinone 4-3 (450 mg, 2.02 mmol) and ammonium chloride (237 mg, 4.44 mmol) in phosphorous oxychloride (2 mL) was heated at reflux for 1.5 h. The reaction mixture was cooled, and the volatiles were removed via rotary evaporation. The residue was quenched with water and solid $Na_2CO_3$ was added until the mixture was basic. This aqueous mixture was extracted with dichloromethane (3×), and the combined organics were dried ($Na_2SO_4$), and concentrated to give 4-4 as an amber oil: $^1H$ NMR ($CDCl_3$) δ 7.60 (s, 1H), 4.87 (s, 2H), 4.32 (q, 2H, 7.1 Hz), 1.31 (t, 3H, 7.1 Hz).

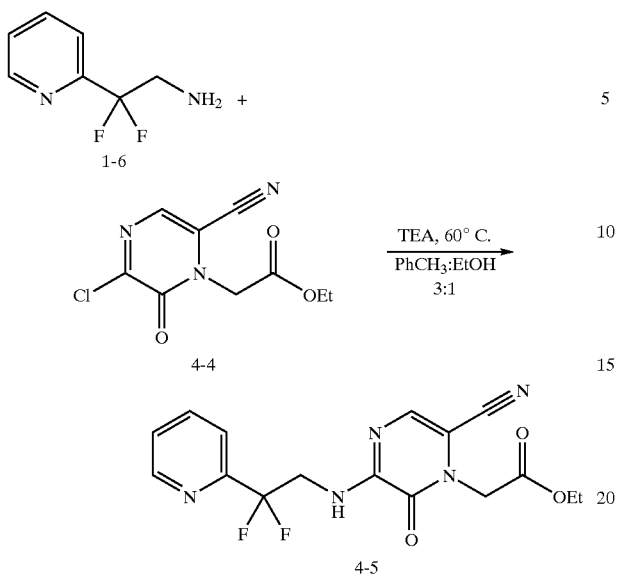

Step E: Ethyl 3-(2,2-Difluoro-2-(2-pyridyl)ethylamino)-6-cyanopyrazin(1H)-2-one-1-acetate (4-5)

A mixture of 0.300 g (1.9 mmol) of 2,2-difluoro-2-(2-pyridyl)ethylamine 1-6, 0.35 mL (2.5 mmol) of triethylamine and 0.42 g (1.75 mmol) of ethyl 3-chloro-6-cyanopyrazin(1H)-2-one-1-acetate 4-4 in 3 mL of toluene and 0.5 mL of ethanol was heated to 60° C. for 1 h. The reaction was concentrated and the residue partitioned between dichloromethane and sat. aq. NaHCO$_3$. The aqueous phase was backwashed with dichloromethane (2×), dried and concentrated. Flash chromatography on silica gel, using 25–50% EtOAc/hexanes afforded 4-5 as a tan powder: $^1$H NMR (CDCl$_3$) δ 8.67 (d, 1H, 4.8 Hz), 7.86 (ddd, 1H, 1.6, 7.8, 7.8 Hz), 7.71 (dd, 1H, 0.9, 8.0 Hz), 7.43 (m, 2H), 7.35 (br t, 1H), 4.79 (s, 2H), 4.62 (dt, 2H, 6.5, 13.5 Hz), 4.29 (q, 2H, 7.1 Hz), 1.32 (t, 3H, 7.1 Hz).

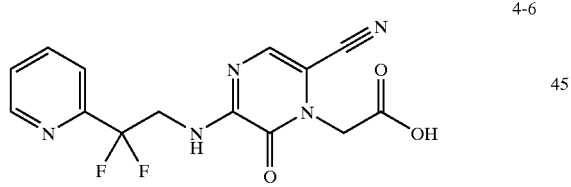

Step F: 3-(2,2-Difluoro-2-(2-pyridyl)ethylamino)-6-cyanopyrazin(1H)-2-one-1-acetic Acid (4-6)

To a stirred solution of 0.38 g (1.06 mmol) of ethyl 3-(2,2-difluoro-2-(2-pyridyl)ethylamino)-6-cyanopyrazin(1H)-2-one-1-acetate 4-5 in dimethoxyethane (10 mL) was added 1.6 mL lithium hydroxide solution (1.0M in water). After 1 h, the solution was neutralized using 1M HCl. Concentration at reduced pressure (azeotrope with PhCH$_3$) afforded an off-white solid containing lithium chloride and 4-6, which was used directly in the next step.

Step G: 3-Fluoro-2-pyridylmethyl 3-(2,2-difluoro-2-(2-pyridyl)ethylamino)-6-15 cyanopyrazin-2-one-1-acetamide Hydrochloride (4-7)

A stirred solution of 0.080 mmol of 3-(2,2-difluoro-2-(2-pyridylethylamino)-6-cyanopyrazin(1H)-2-one-1-acetic acid 4-6 and 24 mg (0.12 mmol) 2-aminomethyl-3-fluoropyridine dihydrochloride in 1 mL of DMF was added 23 mg (0.12 mmol) of EDC, 16 mg (0.12 mmol) of HOAT and 0.056 mL (0.40 mmol) triethylamine. After stirring for 24 h, 20 mg of 2-aminomethyl-3-fluoropyridine dihydrochloride, 25 mg of EDC, and 0.050 mL triethylamine were added. The reaction was stirred for an additional 72 h and the volatiles were removed en vacuo. The residue was diluted with sat. aq. NaHCO$_3$ (5 mL) and water (5 mL) and filtered to afford a tan solid. This material was chromatographed on SiO$_2$ using 2:98 to 4:96 MeOH-CH$_2$Cl$_2$ to give a yellow solid 4-7: $^1$H NMR (CDCl$_3$) δ 8.66 (d, 1H, 4.8 Hz), 8.34 (dd, 1H, 1, 4.8 Hz), 7.84 (ddd, 1H, 1.5, 7.8, 7.8 Hz), 7.70 (dd, 1H, 1, 7.9 Hz), 7.44–7.39 (m, 3H), 7.33 (m, 2H), 7.26 (m, 2H), 4.83 (s, 2H), 4.68 (d, 2H, 4.4 Hz), 4.44 (dt, 2H, 6.5, 13.1 Hz).

EXAMPLE 5

Preparation of 3-Fluoro-4-methyl-2-pyridylmethyl 3-(2,2-difluoro-2-(2-pyridyl)ethylamino)-6-chloropyrazin-2-one-1-acetamide (5-5)

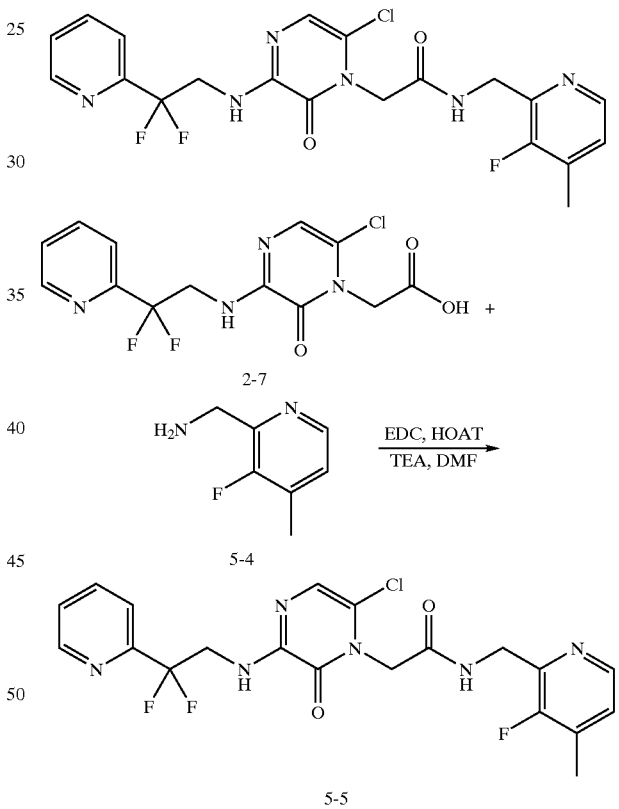

3-Fluoro-4-methylpyridine (5-1)

To a stirred solution of LDA (5.5 mmol) at −78° C., was added 3-fluoropyridine (486 mg, 5.0 mmol) dropwise. After stirring for 4h at −78° C., methyl iodide was added dropwise (0.343 mL, 5.5 mmol). The reaction was quenched after stirring at −78° C. for 2 h, by the addition of 20 mL of sat. aq. NH$_4$Cl. This mixture was extracted with EtOAc (3×25 mL), the combined organics dried and concentrated to afford the product as a yellow solid 5-1: $^1$H NMR (CDCl$_3$) δ 8.36 (br s, 1H), 8.27 (d, 1H, 4.8 Hz), 7.15 (br dd, 1H, 5.7, 5.7 Hz), 2.32 (s, 3H).

3-Fluoro-4-methylpyridine-N-oxide. (5-2)

To a stirred solution of 3.17 g (28.6 mmol) of 3-fluoro-4-methylpyridine in 5-1 35 mL of dichloromethane was added 4.83 g NaHCO$_3$ (57.5 mmol, in 10 mL H$_2$O). This mixture was cooled to 0° C., and 9.85 g of MCPBA (57.1 mmol) was added in three portions over 15 min. The reaction was allowed to warm to room temperature overnight. The layers of the biphasic mixture were separated and the aqueous phase was washed with chloroform (3×100 mL). The combined organic layers were dried over MgSO$_4$ and the solvents removed at reduced pressure to give an oil that was chromatographed on SiO$_2$ using 95:5 DCM-MeOH to give 5-2 as a white solid: $^1$H NMR (CDCl$_3$) δ 8.13 (d, 1H, 4.6 Hz), 7.99 (d, 1H, 6.6 Hz), 7.09 (br dd, 1H, 7.6, 7.6 Hz), 2.30 (s, 3H).

2-Cyano-3-fluoro-4-methylpyridine (5-3)

To a stirred solution of 0.95 g (7.48 mmol) of 3-fluoro-4-methylpyridine N-oxide 5-2 in 20 mL of acetonitrile was added 1.14 g (11.2 mmol) of triethylamine followed by 1.48 g (15.0 mmol) of trimethylsilyl cyanide. This reaction mixture was heated at reflux for 48 h, after which time the solution was concentrated at reduced pressure. The dark residue was dissolved in CHCl$_3$, washed with saturated aqueous NaHCO$_3$ and the aqueous layer back-washed with chloroform (4×). The combined organic layers were dried over MgSO$_4$ and the solvents removed at reduced pressure to give an oil that was chromatographed on SiO$_2$ using 75:25 hexane-EtOAc to give 5-3 as a yellow oil: $^1$H NMR (CDCl$_3$) δ 8.39 (d, 1H, 4.8 Hz), 7.09 (br dd, 1H, 5.8, 5.8 Hz), 2.41 (s, 3H).

2-Aminomethyl-3-fluoro-4-methylpyridine Dihydrochloride (5-4)

A stirred solution of 332 mg (2.44 mmol) of 2-cyano-3-fluoro4-methylpyridine 5-3 in 15 mL of ethanol and 0.61 mL (7.32 mmol) of conc. HCl was hydrogenated over 175 mg of 10% palladium on carbon at 55 psi for 16 h. The catalyst was removed by filtration and the solvents removed at reduced pressure to give 5-4 as a yellow solid: $^1$H NMR (CD$_3$OD) δ 8.41 (d, 1H, 5.1 Hz), 7.54 (dd, 1H, 5.5, 5.5 Hz), 4.40 (s, 2H), 2.44 (s, 3H).

3-Fluoro-4-methyl-2-pyridylmethyl 3-(2,2-difluoro-2-(2-pyridyl)ethylamino)-6-chloropyrazin-2-one-1-acetamide (5-5)

A stirred solution of 80 mg (0.197 mmol, remainder KCl) of 3-(2,2-difluoro-2-(2-pyridyl)ethylamino)-6-chloropyrazin(1H)-2-one-1-acetic acid 2-7 and 63 mg (0.296 mmol) 2-aminomethyl-3-fluoro-4-methylpyridine dihydrochloride 5-4 in 1 mL of DMF was added 77 mg (0.40 mmol) of EDC, 54 mg (0.40 mmol) of HOAT and 0.13 mL (0.89 mmol) TEA. After stirring overnight, the volatiles were removed en vacuo. The residue was diluted with sat. aq. NaHCO$_3$, filtered, and rinsed with water to afford a brown solid. This material was flash chromatographed using 2–4% MeOH:DCM to afford the title compound as a white solid. Conversion to the HCl salt was accomplished by diluting the free base with MeOH (5 mL), treating with 2.5M HCl (2 mL) and concentrating to a solid 5-5: $^1$H NMR (CD$_3$OD) δ 8.82 (d, 1H, 4.1 Hz), 8.56 (d, 1H, 5.1 Hz), 8.33 (dd, 1H, 7.4, 7.4 Hz), 8.04 (d, 1H, 7.8 Hz), 8.00 (br t, 1H), 7.87 (br t, 1H, 5.6 Hz), 6.92 (s, 1H), 5.0 (s, 2H), 4.80 (s, 2H), 4.44 (t, 2H, 1.36 Hz), 2.621 (s, 3H).

Typical tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Suggested Ranges of Composition for Excipients in Uncoated Tablet Cores

Mannitol, microcrystalline cellulose and magnesium stearate may be substituted with alternative pharmaceutically acceptable excipients.

The following synthetic methods can be used to prepare the compounds of the present invention:

In Vitro Assay For Determining Proteinase Inhibition

Assays of human α-thrombin and human trypsin were performed by the methods substantially as described in Thrombosis Research, Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration≦0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1.

$$V_o/V_i = 1 + [I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Inhibitory activity of compounds of the invention, represented by "**", indicating Ki greater than or equal to 1 nM, or "*", indicating Ki less than 1 nM, and measured using the above assay, is shown above.

EXAMPLE 6

Tablet Preparation

Tablets containing 8, 10, 20 and 40 mg., respectively, of the following active compounds are prepared as illustrated below (compositions A-C). Active I is selected from the group of compounds including 1-9 (3-Fluoro-2-pyridylmethyl-3-(2,2-difluoro-2-[2-pyridyl)ethylamino)-6-methyl pyrazin-2-one-1-acetamide) compound 2-8 (3-Fluoro-2-pyridylmethyl-3-(2,2-difluoro-2-(2-pyridyl) ethylamino)-6-chloropyrazin-2-one-1-acetamide), 3-5 ([R, S] 3-Methylsulfinyl-2-pyridylmethyl-3-(2,2-difluoro-2-(2-pyridyl)ethylamino)-6-chloropyrazin-2-one-1-acetamide), 4-7 ( 3-Fluoro-2-pyridylmethyl 3-(2,2-difluoro-2-(2-pyridyl)ethylamino)-6-cyanopyrazin-2-one-1-acetamide hydrochloride) and 5-5 (3-Fluoro-4-methyl-2-pyridylmethyl 3-(2,2-difluoro-2-(2-pyridyl)ethylamino)-6-chloropyrazin-2-one-1-acetamide). Amounts shown are free base amounts.

Table for Doses Containing from 8 to 40 mg of the Active Compound

|  | Amount-mg | | | |
| --- | --- | --- | --- | --- |
| Component | A | B | C | D |
| Active I | 8 | 10 | 20 | 40 |
| Microcrystalline cellulose | 37.25 | 100 | 200 | 200 |
| Modified food corn starch | 37.25 | 4.25 | 8.5 | 8.5 |
| Magnesium stearate | 0.5 | 0.75 | 1.5 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 7

Tablet Preparation

Exemplary compositions of Active I tablets are shown below:

| Component | 0.25 mg | 2 mg | 10 mg | 50 mg |
| --- | --- | --- | --- | --- |
| Active I | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

In the table, for example, a tablet containing 2 mg of Active I includes 98.5 mg mannitol, 98.5 mg microcrystalline cellulose, and 1 mg magnesium stearate. 2, 10 and 50 mg tablets were film-coated with an aqueous dispersion of hydroxypropyl cellulose, hydroxypropyl methylcellulose and titanium dioxide, providing a nominal weight gain.

Tablet Preparation Via Direct Compression

Active I, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation Via Dry Granulation

Alternatively, a dry powder blend is compacted under modest forces and remilled to afford granules of specified particle size. The granules are then mixed with magnesium stearate and tabletted as stated above.

EXAMPLE 8

Intravenous Formulations

Intravenous formulations of Active I were prepared according to general intravenous formulation procedures.

| Component | Estimated range |
| --- | --- |
| Active I | 0.12–0.61 mg |
| D-glucuronic acid* | 0.5–5 mg |
| Mannitol NF | 50–53 mg |
| 1N Sodium Hydroxide | q.s. pH 3.9–4.1 |
| Water for injection | q.s. 1.0 mL |

Exemplary compositions A–C are as follows:

| Component | A | B | C |
| --- | --- | --- | --- |
| Active I | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:
1. A compound having the formula:

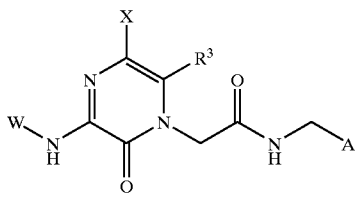

wherein
W is selected from the group consisting of
1) hydrogen,
2) a 5- to 7-membered mono- or a 9- to 10-membered fused bicyclic heterocyclic ring having carbon ring atoms and heteroatom ring atoms which ring can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
      i) $C_{1-4}$ alkyl,
      ii) hydroxy,
      iii) COOR', where R' is hydrogen or $C_{1-4}$ alkyl,
      iv) $CONH_2$,
      v) $CH_2OH$,
      vi) $SO_2NH_2$,
      vii) halogen,
      viii) amino,
      ix) aryl,
      x) $C_{3-7}$ cycloalkyl,
      xi) $CF_3$,
      xiii) $OCF_3$,
      xiii) $N(CH_3)_2$,
      xiv) —$C_{1-3}$alkylaryl,
      xv) heterocyclic ring,
      xvi) $C_{1-4}$ alkoxy,
      xvii) $F_wH_xC(CH_2)_{0-1}$ O—, wherein w and x are either 1 or 2, provided that when w is 1, x is 2, and when w is 2, x is 1,
      xviii) $C_{1-4}$ thioalkoxy, or
      xix) cyano,
3) a 5- to 7-membered mono- or a 9- to 10-membered fused bicyclic non-heterocyclic saturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1,
   r) $C_{1-4}$ thioalkoxy, or
   s) cyano,
4) a 6-membered mono or 9- to 10-membered fused bicyclic non-heterocyclic unsaturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1,
   r) $C_{1-4}$ thioalkoxy, or
   s) cyano,
5) $CF_3$,
6) $C_{3-7}$ cycloalkyl, unsubstituted, monosubstituted with halogen or aryl, or disubstituted with halogen,
7) $C_{7-12}$ bicyclic alkyl,
8) $C_{10-16}$ tricyclic alkyl,
9)

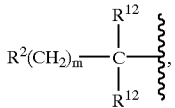

where m is 0–3, and each $R^{12}$ can be the same or different,
10)

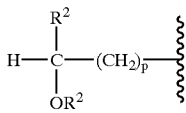

where p is 1–4,
11)

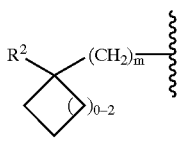

where m is 0–3,

12)

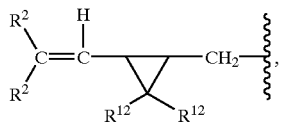

13)

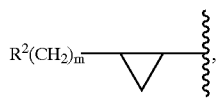

where m is 0 or 1,

14)

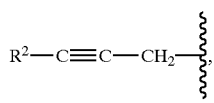

15)

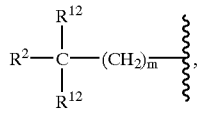

wherein m is 0–3, and each $R^{12}$ can be the same or different, wherein the $R^{12}$ substituents can together form a ring, with the C to which they are bonded, represented by $C_{3-7}$ cycloalkyl,

16)

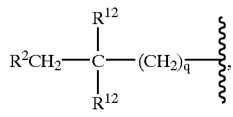

wherein q is 0–2, and each $R^{12}$ can be the same or different, wherein the $R^{12}$ substituents can together form a ring, with the C to which they are bonded, represented by $C_{3-7}$ cycloalkyl,

17)

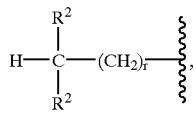

wherein r is 0–4, and each $R^2$ can be the same or different, wherein the $R^2$ substituents can together form a ring, with the C to which they are bonded, represented by $C_{3-7}$ cycloalkyl, $C_{7-12}$ bicyclic alkyl, $C_{10-16}$ tricyclic alkyl, or a 5- to 7-membered mono- or 9- to 10-membered fused bicyclic heterocyclic ring, which can be saturated or unsaturated, and which contains from one to three heteroatoms selected from the group consisting of N, O and S,

18)

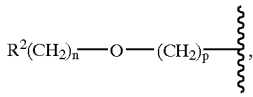

wherein n and p are independently 1–4,

19)

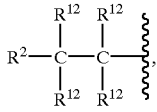

wherein each $R^{12}$ can be the same or different,

20)

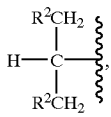

21) and

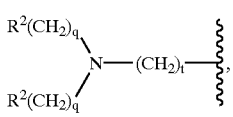

wherein t is 1–4 and q is independently 0–2;

$R^2$ is selected from the group consisting of
1) hydrogen,
2) a 5- to 7-membered mono- or a 9- to 10-membered fused bicyclic heterocyclic ring having carbon ring atoms and heteroatom ring atoms which ring can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
      i) $C_{1-4}$ alkyl,
      ii) hydroxy,
      iii) COOR', where R' is hydrogen or $C_{1-4}$ alkyl,
      iv) $CONH_2$,
      v) $CH_2OH$,
      vi) $SO_2NH_2$,
      vii) halogen,
      viii) amino,
      ix) aryl,
      x) $C_{3-7}$ cycloalkyl,
      xi) $CF_3$,
      xii) $OCF_3$,
      xiii) $N(CH_3)_2$,
      xiv) —$C_{1-3}$alkylaryl,
      xv) heterocyclic ring,
      xvi) $C_{1-4}$ alkoxy,
      xvii) $F_wH_xC(CH_2)_{0-1}O$—, wherein w and x are either 1 or 2, provided that when w is 1, x is 2, and when w is 2, x is 1,
      xviii) $C_{1-4}$ thioalkoxy, or
      xix) cyano, 3) a 5- to 7-membered mono- or a 9- to 10-membered fused bicyclic non-heterocyclic saturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1,
   r) $C_{1-4}$ thioalkoxy, or
   s) cyano,
4) a 6-membered mono or 9- to 10-membered fused bicyclic non-heterocyclic unsaturated ring which is unsubstituted or substituted with one or more of
   a) $C_{1-4}$ alkyl,
   b) hydroxy,
   c) COOR', where R' is hydrogen or $C_{1-4}$ alkyl,
   d) $CONH_2$,
   e) $CH_2OH$,
   f) $SO_2NH_2$,
   g) halogen,
   h) amino,
   i) aryl,
   j) $C_{3-7}$ cycloalkyl,
   k) $CF_3$,
   l) $OCF_3$,
   m) $N(CH_3)_2$,
   n) —$C_{1-3}$alkylaryl,
   o) heterocyclic ring,
   p) $C_{1-4}$ alkoxy,
   q) $F_wH_xC(CH_2)_{0-1}$ O—, wherein w and x are either 1 or 2, provided that when w is 1, x is 2, and when w is 2, x is 1,
   r) $C_{1-4}$ thioalkoxy, or
   s) cyano,
5) $C_{1-7}$ alkyl, unsubstituted or substituted with one or more of
   a) hydroxy,
   b) COOH,
   c) halogen,
   d) amino,
   e) aryl,
   f) $C_{3-7}$ cycloalkyl,
   g) $CF_3$,
   h) $N(CH_3)_2$,
   i) —$C_{1-3}$alkylaryl,
   j) heterocyclic ring,
   k) $C_{1-4}$ alkoxy,
   l) $C_{1-4}$ thioalkoxy, or
   m) cyano,
6) $CF_3$,
7) $C_{3-7}$ cycloalkyl, unsubstituted, monosubstituted with halogen or aryl, or disubstituted with halogen,
8) $C_{7-12}$ bicyclic alkyl, or
9) $C_{10-16}$ tricyclic alkyl;

$R^3$ and X are independently selected from the group consisting of
1) hydrogen,
2) halogen,
3) cyano,
4) $C_{1-4}$ alkylthio,
5) $C_{1-4}$ alkylsulfinyl,
6) $C_{1-4}$ alkylsulfonyl,
7) $C_{1-4}$ alkyl,
8) $C_{3-7}$ cycloalkyl, and
9) trifluoromethyl;

A is

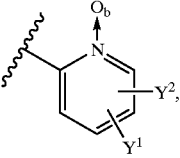 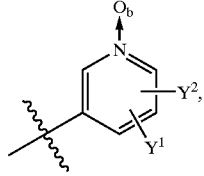

or

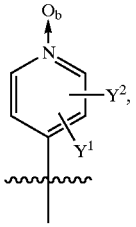

wherein $Y^1$ and $Y^2$ are independently selected from the group consisting of
1) hydrogen,
2) $C_{1-4}$ alkyl,
3) $C_{1-4}$ alkoxy,
4) $F_uH_vC(CH_2)_{0-1}$ O—, wherein u and v are either 1 or 2, provided that when u is 1, v is 2, and when u is 2, v is 1,
5) $C_{3-7}$ cycloalkyl,
6) $C_{1-4}$ alkylthio,
7) $C_{1-4}$ alkylsulfinyl,
8) $C_{1-4}$ alkylsulfonyl,
9) halogen
10) cyano, and
11) trifluoromethyl, and
wherein b is 0 or 1; and $R^{12}$ is selected from the group consisting of
1) hydrogen,
2) halogen,
3) a 5- to 7-membered mono- or a 9- to 10-membered fused bicyclic heterocyclic ring having carbon ring atoms and heteroatom ring atoms which ring can be saturated or unsaturated, wherein the ring contains
   a) from one to four heteroatoms selected from the group consisting of N, O and S, and wherein the ring is unsubstituted, or
   b) from one to four N atoms, and where one or more of the ring atoms are substituted with one or more of
      i) $C_{1-4}$ alkyl,
      ii) hydroxy,
      iii) COOR', where R' is, hydrogen or $C_{1-4}$ alkyl,
      iv) $CONH_2$,
      v) $CH_2OH$, vi) $SO_2NH_2$,
vii) halogen,
viii) amino,
ix) aryl,
x) $C_{3-7}$ cycloalkyl,
xi) $CF_3$,
xii) $OCF_3$,
xiii) $N(CH_3)_2$,
xiv) —$C_{1-3}$alkylaryl,
xv) heterocyclic ring,
xvi) $C_{1-4}$ alkoxy,
xvii) $F_wH_xC(CH_2)_{0-1}$ O—, wherein w and x are either 1 or 2, provided that when w is 1, x is 2, and when w is 2, x is 1,
xviii) $C_{1-4}$ thioalkoxy, and
xix) cyano,
4) a 5- to 7-membered mono- or a 9- to 10-membered fused bicyclic non-heterocyclic saturated ring which is unsubstituted or substituted with one or more of
a) $C_{1-4}$ alkyl,
b) hydroxy,
c) COOR', where R' is hydrogen or $C_{1-4}$ alkyl,
d) $CONH_2$,
e) $CH_2OH$,
f) $SO_2NH_2$,
g) halogen,
h) amino,
i) aryl,
j) $C_{3-7}$ cycloalkyl,
k) $CF_3$,
l) $OCF_3$,
m) $N(CH_3)_2$,
n) —$C_{1-3}$alkylaryl,
o) heterocyclic ring,
p) $C_{1-4}$ alkoxy,
q) $F_wH_xC(CH_2)_{0-1}$ O—, wherein w and x are either 1 or 2, provided that when w is 1, x is 2, and when w is 2, x is 1,
r) $C_{1-4}$ thioalkoxy, or
s) cyano,
5) a 6-membered mono or 9- to 10-membered fused bicyclic non-heterocyclic unsaturated ring which is unsubstituted or substituted with one or more of
a) $C_{1-4}$ alkyl,
b) hydroxy,
c) COOR', where R' is hydrogen or $C_{1-4}$ alkyl,
d) $CONH_2$,
e) $CH_2OH$,
f) $SO_2NH_2$,
g) halogen,
h) amino,
i) aryl,
j) $C_{3-7}$ cycloalkyl,
k) $CF_3$,
l) $OCF_3$,
m) $N(CH_3)_2$,
n) —$C_{1-3}$alkylaryl,
o) heterocyclic ring,
p) $C_{1-4}$ alkoxy,
q) $F_wH_xC(CH_2)_{0-1}$ O—, wherein w and x are either 1 or 2, provided that when w is 1, x is 2, and when w is 2, x is 1,
r) $C_{1-4}$ thioalkoxy, or
s) cyano, 6) biphenyl,
7) $CF_3$,
8) $C_{3-7}$ cycloalkyl,
9) $C_{7-12}$ bicyclic alkyl, and
10) $C_{10-16}$ tricyclic alkyl;
or a pharmaceutically acceptable salt thereof.

2. A compound of claim 1, or pharmaceutically acceptable salt thereof, wherein $Y^1$ and $Y^2$ are independently selected from the group consisting of hydrogen, $C_{1-4}$ alkyl, halogen, $C_{1-4}$ alkylthio, $C_{1-4}$ alkylsulfinyl, $C_{1-4}$ alkylsulfonyl, and $C_{1-4}$ alkoxy.

3. A compound of claim 2, or pharmaceutically acceptable salt thereof, wherein $Y^1$ and $Y^2$ are independently selected from the group consisting of hydrogen, F, $CH_3$, $SCH_3$, $SOCH_3$, $SO_2CH_3$, and $OCH_3$.

4. A compound of claim 3, or pharmaceutically acceptable salt thereof, wherein A is selected from the group consisting of where b is 0 or 1.

5. A compound of claim 4, or pharmaceutically acceptable salt thereof, wherein X is hydrogen, $R^3$ is $CH_3$, Cl or CN, and W is $R^2CF_2C(R^{12})_2$ or $R^2CH_2C(R^{12})_2$.

6. A compound of claim 5, or pharmaceutically acceptable salt thereof, wherein $R^{12}$ is hydrogen.

7. A compound of claim 6, or a pharmaceutically acceptable salt thereof, wherein $R^2$ is selected from the group consisting of 1) a 5- to 7-membered mono- or a 9- to 10-membered fused bicyclic heterocyclic ring having carbon ring atoms and heteroatom ring atoms which ring can be saturated or unsaturated, wherein the ring contains
a) from one to four heteroatoms selected from the group consisting of N, O and S, and wherein the ring is unsubstituted, or
b) from one to four N atoms, and where one or more of the ring atoms are substituted with one or more of
i) $C_{1-4}$ alkyl,
ii) hydroxy, iii) COOR', where R' is hydrogen or $C_{1-4}$ alkyl,
iv) $CONH_2$,
v) $CH_2OH$,
vi) $SO_2NH_2$,
vii) halogen,
viii) amino,
ix) aryl,
x) $C_{3-7}$ cycloalkyl,
xi) $CF_3$,
xii) $OCF_3$,
xiii) $N(CH_3)_2$,
xiv) —$C_{1-3}$alkylaryl,
xv) heterocyclic ring,
xvi) $C_{1-4}$ alkoxy,
xvii) $F_wH_xC(CH_2)_{0-1}$ O—, wherein w and x are either 1 or 2, provided that when w is 1, x is 2, and when w is 2, x is 1,
xviii) $C_{1-4}$ thioalkoxy, or
xix) cyano, and 2) a 6-membered mono or 9- to 10-membered fused bicyclic non-heterocyclic unsaturated ring which is unsubstituted or substituted with one or more of
a) $C_{1-4}$ alkyl,
b) hydroxy,
c) COOR', where R' is hydrogen or $C_{1-4}$ alkyl,
d) $CONH_2$,
e) $CH_2OH$,
f) $SO_2NH_2$,
g) halogen,
h) amino,
i) aryl,
j) $C_{3-7}$ cycloalkyl,
k) $CF_3$,
l) $OCF_3$,
m) $N(CH_3)_2$,
n) —$C_{1-3}$alkylaryl,
o) heterocyclic ring,
p) $C_{1-4}$ alkoxy,
q) $F_wH_xC(CH_2)_{0-1}$ O—, wherein w and x are either 1 or 2, provided that when w is 1, x is 2, and when w is 2, x is 1,
r) $C_{1-4}$ thioalkoxy, or
s) cyano.

8. A compound of claim 7, or pharmaceutically acceptable salt thereof, wherein $R^2$ is pyridyl, methoxypyridyl, or phenyl.

9. A compound of claim 8, or pharmaceutically acceptable salt thereof, selected from the group consisting of:

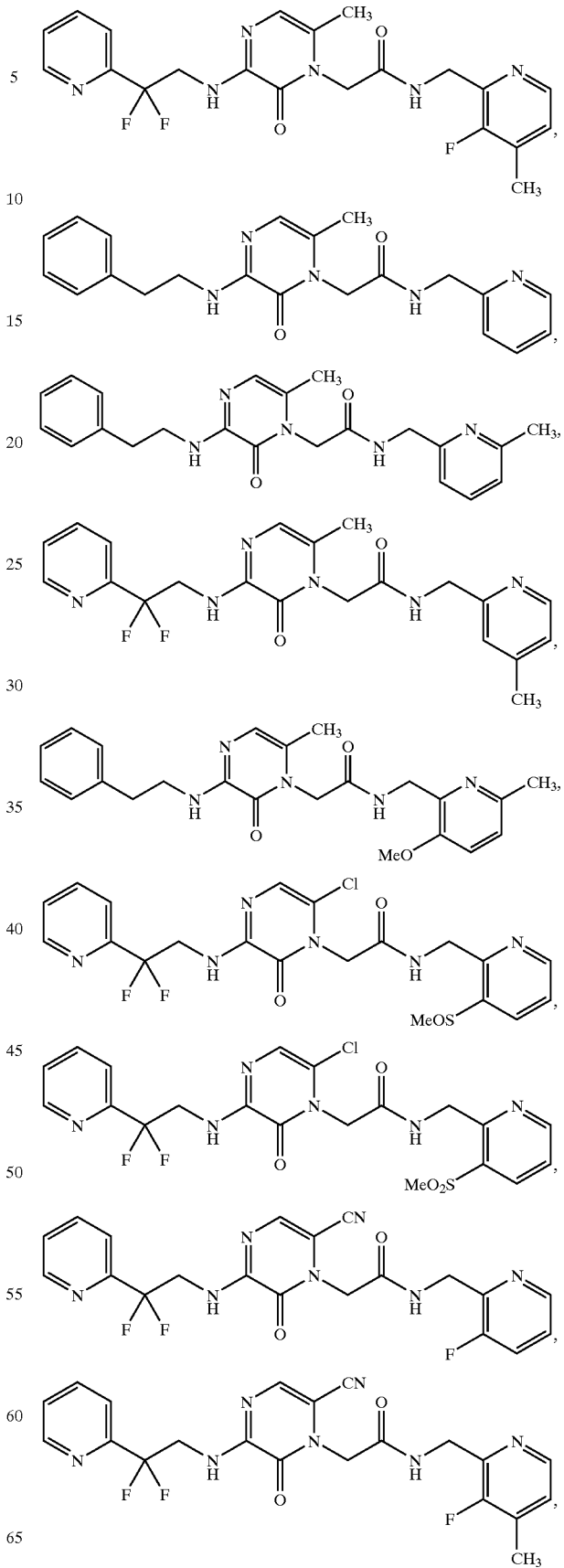

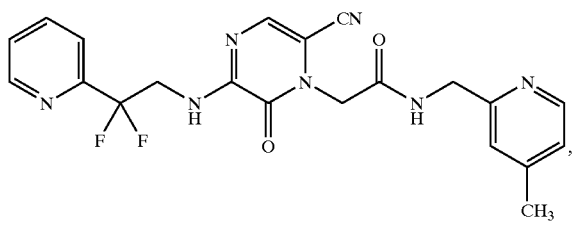
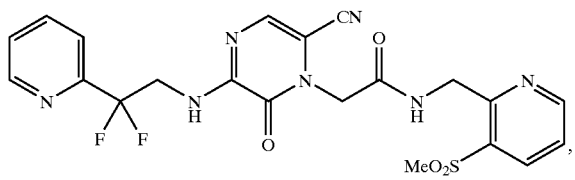
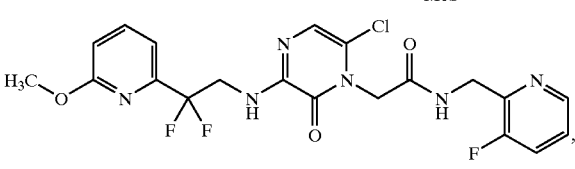
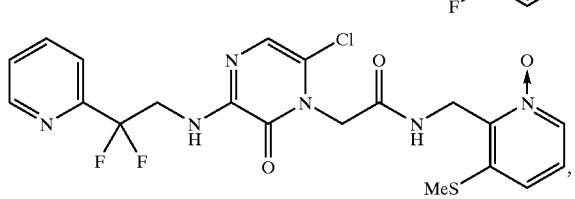
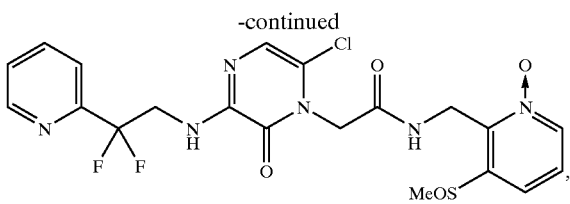
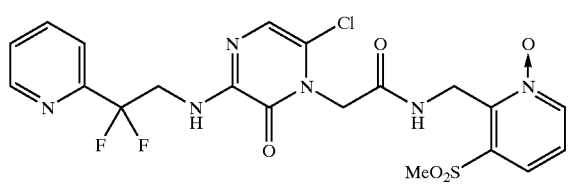
or a pharmaceutically acceptable salt thereof.
10. A compound of claim 9, or pharmaceutically acceptable salt thereof, which is
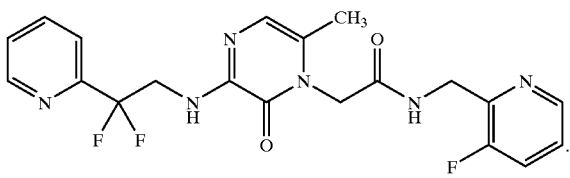
11. A compound of claim 9, or pharmaceutically acceptable salt thereof, which is
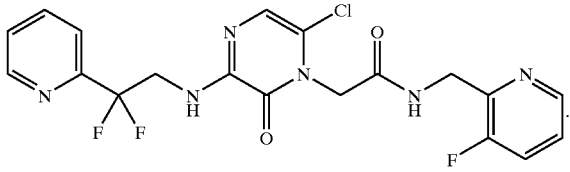
12. A compound of claim 9, or pharmaceutically acceptable salt thereof, which is
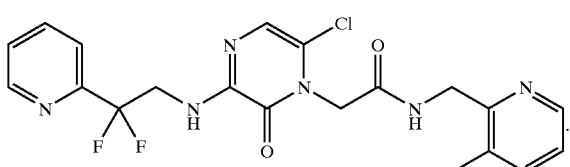
13. A compound of claim 9, or pharmaceutically acceptable salt thereof, which is
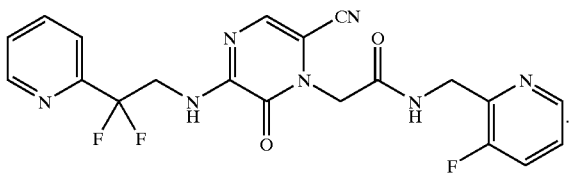

14. A compound of claim 9, or pharmaceutically acceptable salt thereof, which is

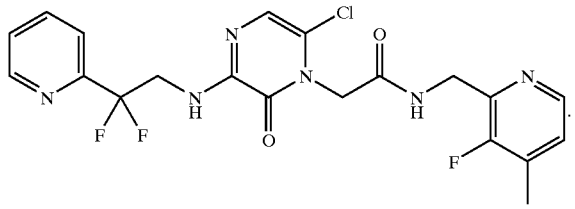

15. An oral pharmaceutical composition comprising a compound of claim 1 and a pharmaceutically acceptable carrier.

16. An intravenous pharmaceutical composition comprising a compound of claim 1 and a pharmaceutically acceptable carrier.

17. A method for inhibiting thrombin in blood comprising adding to the blood a compound of claim 1.

18. A method for inhibiting formation of blood platelet aggregates in blood comprising adding to the blood a compound of claim 1.

19. A method for inhibiting thrombus formation in blood comprising adding to the blood a compound of claim 1.

20. A method for treating or preventing venous thromboembolism and pulmonary embolism in a mammal comprising administering to the mammal a composition of claim 15.

21. A method for treating or preventing deep vein thrombosis in a mammal comprising administering to the mammal a composition of claim 15.

22. A method for treating or preventing cardiogenic thromboembolism in a mammal comprising administering to the mammal a composition of claim 15.

23. A method for treating or preventing thromboembolic stroke in humans and other mammals comprising administering to the mammal a composition of claim 15.

24. A method for treating or preventing thrombosis associated with cancer and cancer chemotherapy in a mammal comprising administering to the mammal a composition of claim 15.

25. A method for treating or preventing unstable angina in a mammal comprising administering to the mammal a composition of claim 15.

* * * * *